(12) United States Patent  (10) Patent No.: US 8,211,032 B2
Schecter et al.  (45) Date of Patent: Jul. 3, 2012

(54) CARDIOMECHANICAL ASSESSMENT FOR CARDIAC RESYNCHRONIZATION THERAPY

(75) Inventors: Stuart O. Schecter, Great Neck, NY (US); Kjell Noren, Solna (SE)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/191,253

(22) Filed: Jul. 26, 2011

(65) Prior Publication Data

US 2011/0306890 A1  Dec. 15, 2011

Related U.S. Application Data

(62) Division of application No. 12/140,862, filed on Jun. 17, 2008, now Pat. No. 8,014,864.

(51) Int. Cl.
*A61B 5/0452* (2006.01)
(52) U.S. Cl. ........................ 600/508; 600/513
(58) Field of Classification Search ............. 607/17, 607/18; 600/513
See application file for complete search history.

(56) References Cited

U.S. PATENT DOCUMENTS

| 6,526,984 | B1 | 3/2003 | Nilsson et al. |
| 7,010,347 | B2 | 3/2006 | Schecter |
| 7,142,919 | B2 | 11/2006 | Hine et al. |
| 2003/0105496 | A1 | 6/2003 | Yu et al. |
| 2006/0178586 | A1 | 8/2006 | Dobak |

FOREIGN PATENT DOCUMENTS

WO  WO 2006/050385  *  5/2006

OTHER PUBLICATIONS

Restriction Requirement, mailed Nov. 15, 2010—U.S. Appl. No. 12/140,862.
NonFinal Office Action, mailed Jan. 12, 2011—U.S. Appl. No. 12/140,862.
Notice of Allowance, mailed Jun. 15, 2011—U.S. Appl. No. 12/140,862.

* cited by examiner

*Primary Examiner* — Michael Kahelin

(57) ABSTRACT

A first lead provides therapeutic stimulation to the heart and includes a first mechanical sensor that measures physical contraction and relaxation of the heart. A controller induces delivery of therapeutic stimulation via the first lead. The controller receives signals from the first mechanical sensor indicative of the contraction and relaxation; develops a template signal that corresponds to the contraction and relaxation; and uses the template signal to modify the delivery of therapeutic stimulations. In another arrangement, a second lead, with a second mechanical sensor also provides signals to the controller indicative of contraction and relaxation. The first mechanical sensor is adapted to be positioned at the interventricular septal region of the heart, and the second mechanical sensor is adapted to be positioned in the lateral region of the left ventricle. The controller processes the signals from the first mechanical sensor and the second mechanical sensor to develop a dysynchrony index.

10 Claims, 21 Drawing Sheets

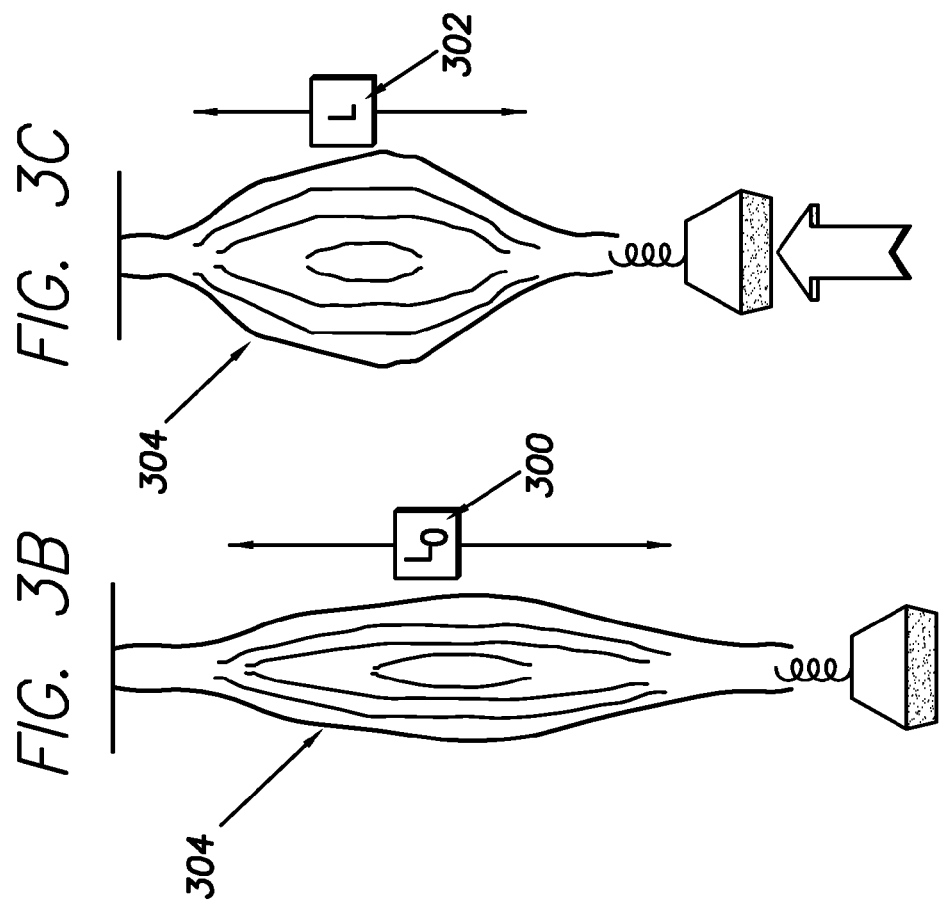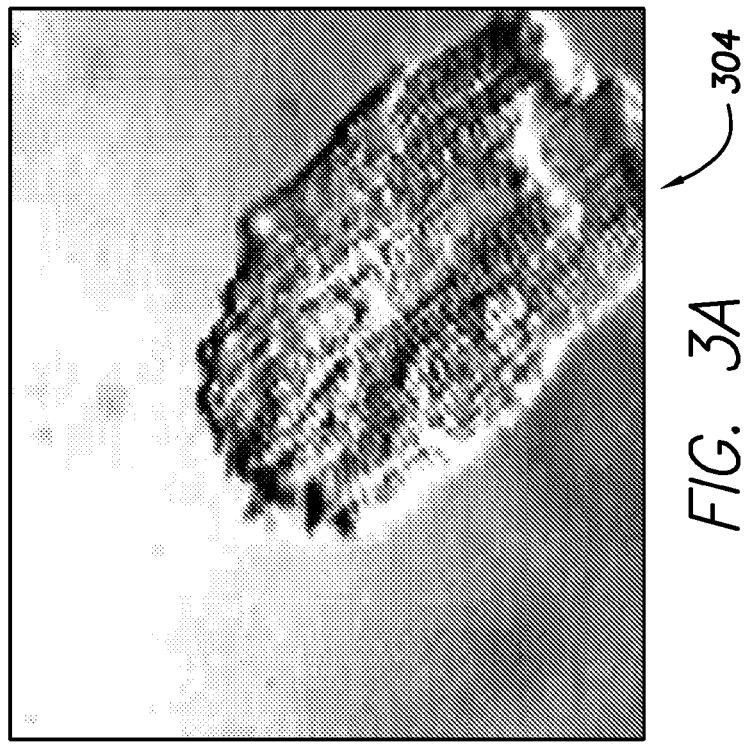

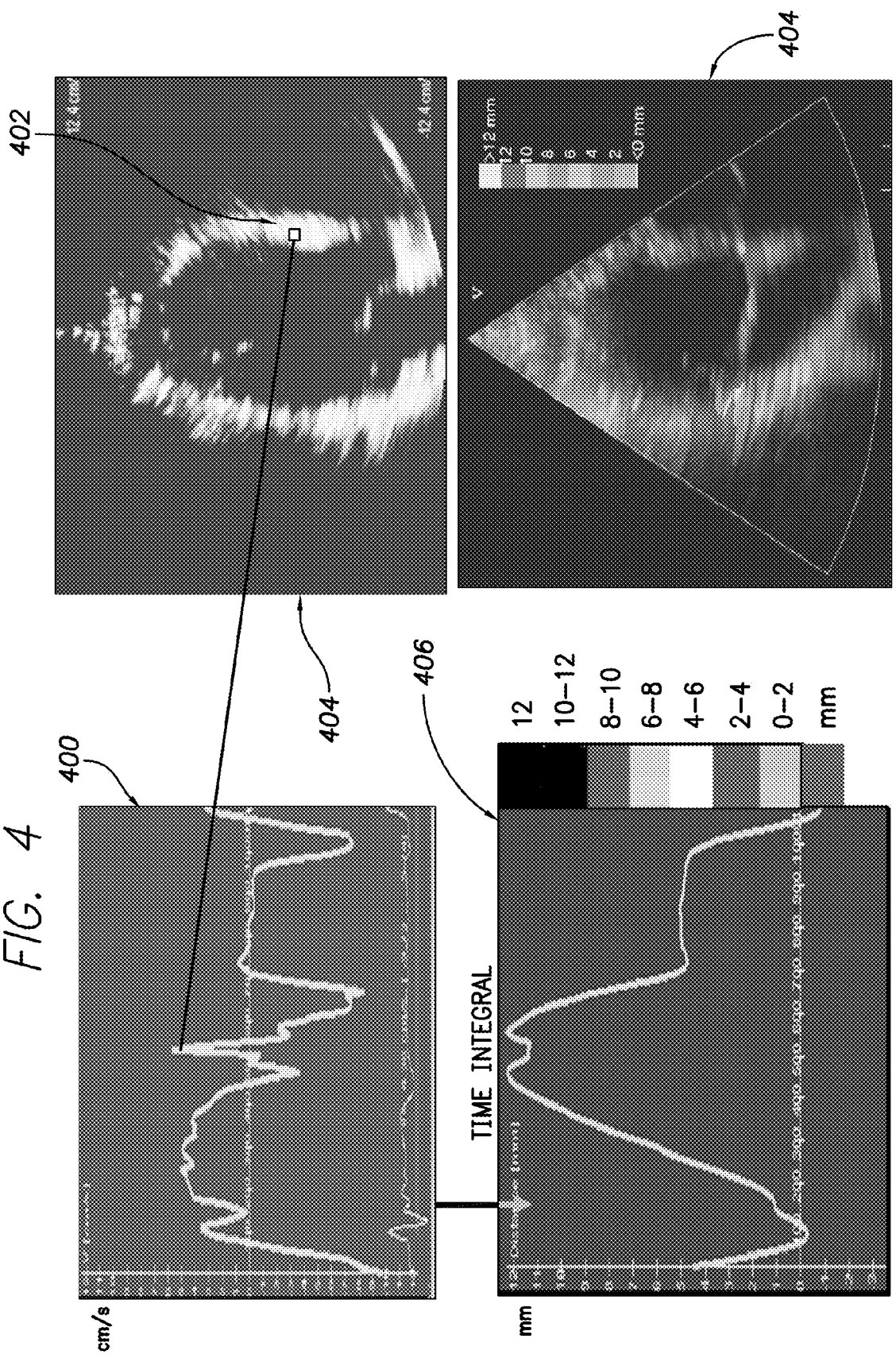

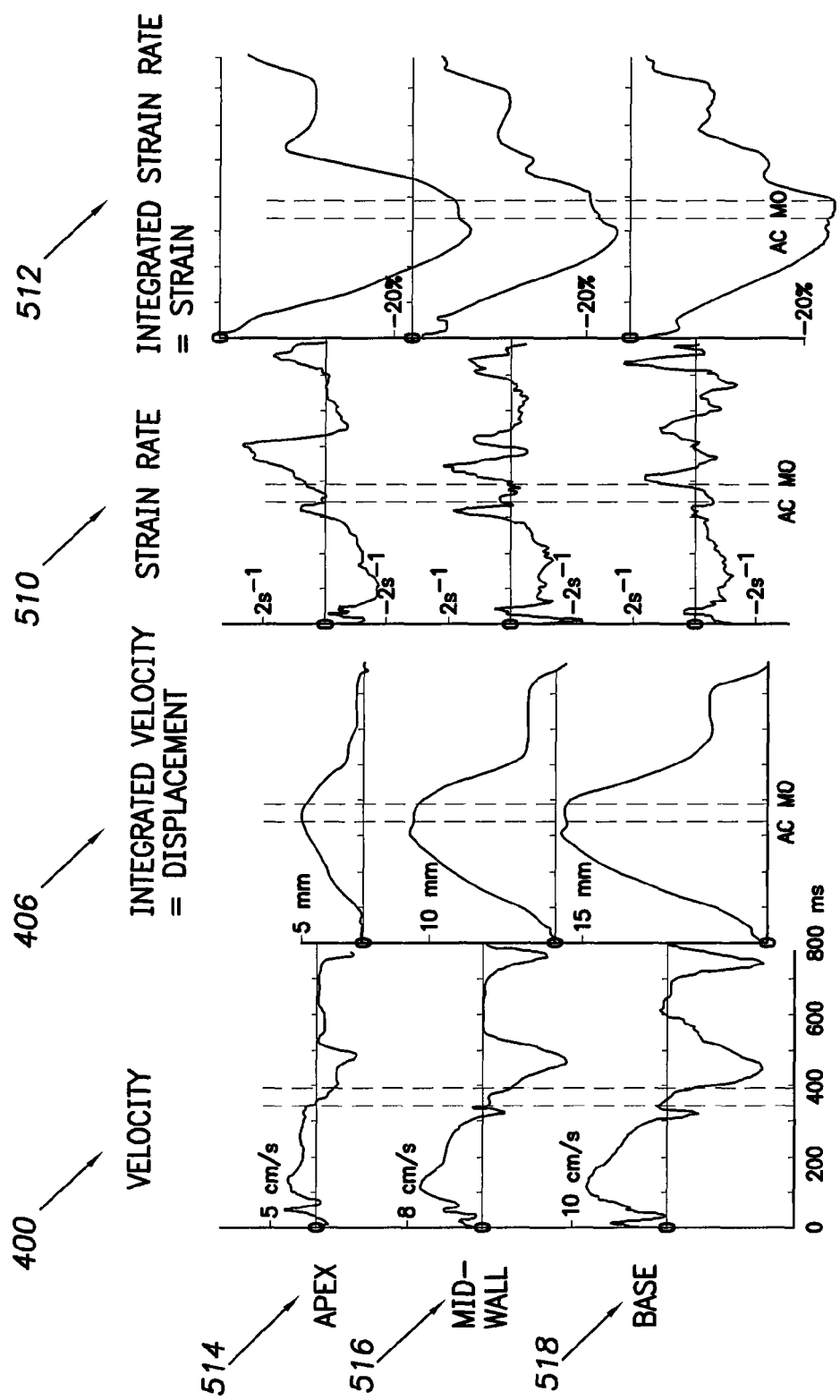

FIG. 10C
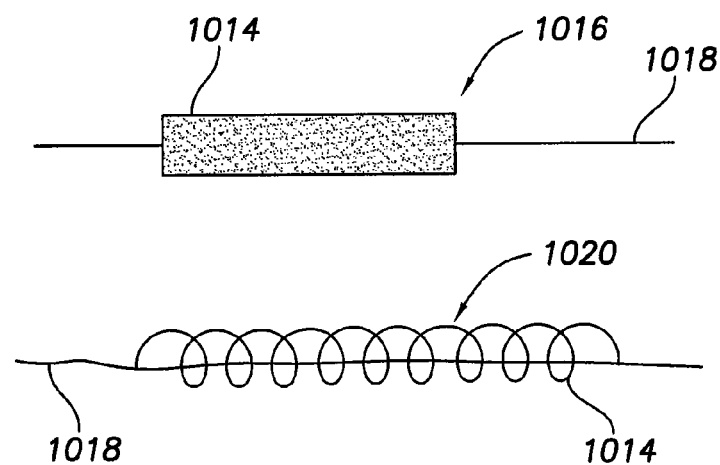
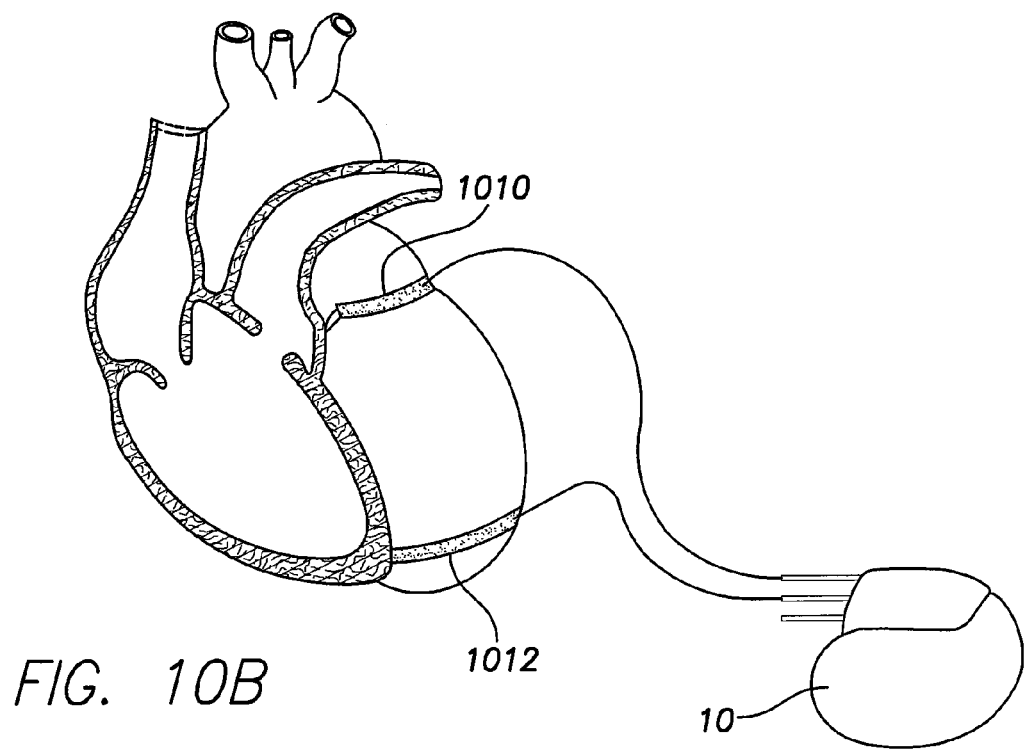
FIG. 10B

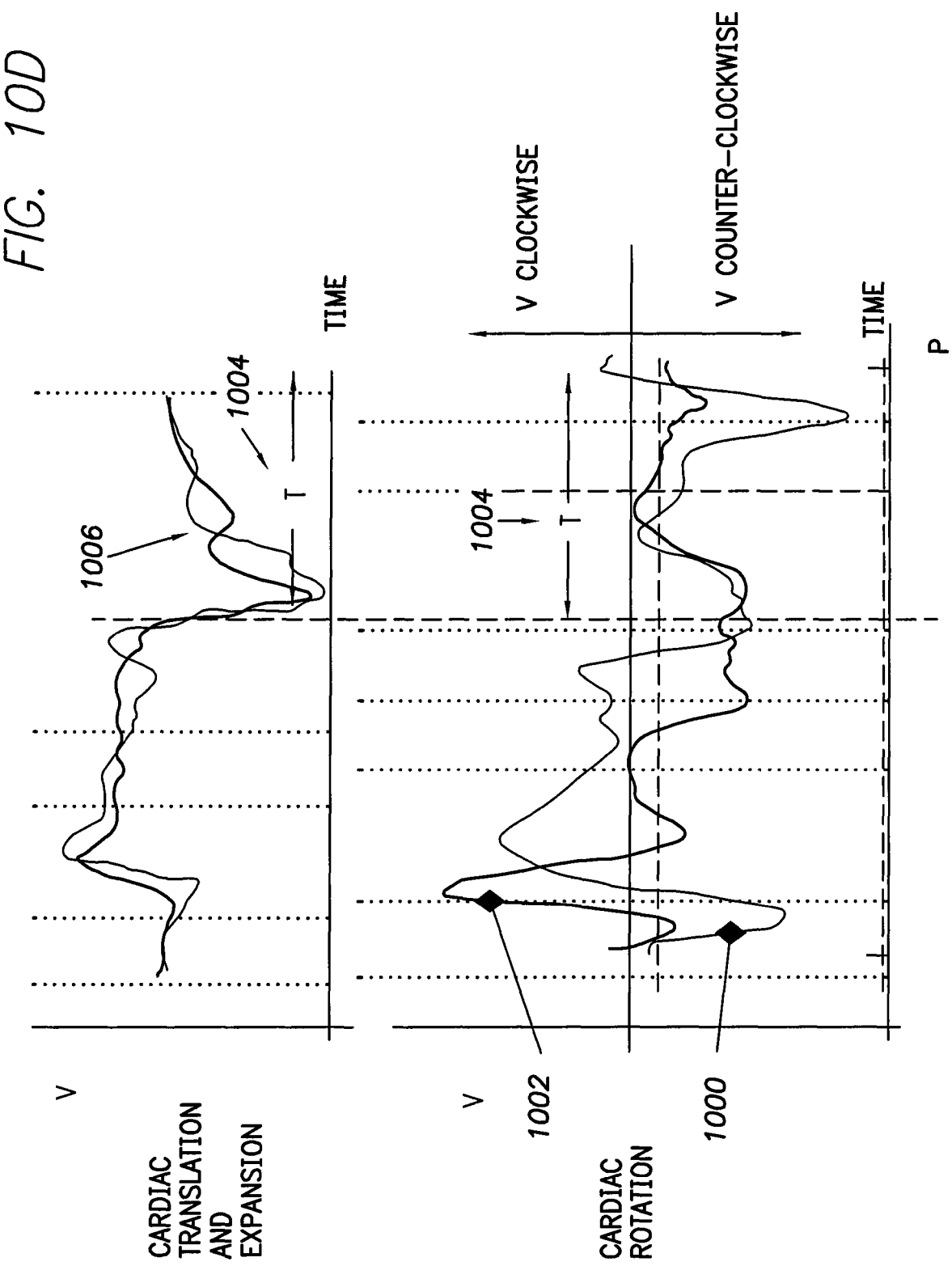

CARDIOMECHANICAL ASSESSMENT FOR CARDIAC RESYNCHRONIZATION THERAPY

CROSS REFERENCE TO RELATED APPLICATIONS

This application is a division of U.S. patent application Ser. No. 12/140,862, filed Jun. 17, 2008, titled "Cardiomechanical Assessment for Cardiac Resynchronization Therapy," now U.S. Pat. No. 8,014,864.

FIELD OF THE INVENTION

The present disclosure relates to an implantable sensor that is capable of measuring longitudinal, radial and torsional strain in the heart. The strain data can be used to improve cardiac resynchronization therapy timings for implantable cardiac stimulation devices and systems.

BACKGROUND

Implantable devices for pacing, cardioversion, defibrillation and resynchronization of cardiac electrical and mechanical function are widely available to prevent and treat arrhythmias and dysynchronous myocardial mechanics. These disorders can impair cardiac performance by altering electrical conduction patterns or by changing myocardial contractility or compliance, both of which result in mechanical dysfunction.

For example, conduction abnormalities may occur between the atria and the ventricular chambers. When atrioventricular (AV) timing is shortened, ventricular contraction may prematurely terminate the atrial kick produced by the contracting atrium. When AV timing is prolonged, increased ventricular loading from the atria may be lost due to regurgitation during prolonged diastole. Thus, both shortened and prolonged AV timing intervals can affect cardiac output.

Conduction abnormalities between right and left ventricular chambers (inter-ventricular) or within the right or left ventricles (intra-ventricular) can also result in dysynchrony. Dysynchrony occurs when forces generated in specific regions at inappropriate times cause bulging of the chamber walls into adjacent relaxed wall segments, or against prematurely closed heart valves. This lack of coordination during myocardial contraction may cause a reduction of forward blood flow and lead to reduced contractile efficiency.

Conduction abnormalities may also result in contractile and compliance abnormalities with cardiac function. For example, conduction delays may cause the left ventricular myocardium to continue to contract even after the closure of the aortic valve. This persistent contractile effect creates post-systolic wall thickening that can reduce left ventricle compliance and cause a reduction in ventricular end-diastolic volume (pre-load). The reduction in pre-load will reduce stroke volume and cardiac output through the Frank-Starling mechanism. Post-systolic wall thickening and post-systolic myocardial motion are also indicative of inefficient cardiac effort occurring against a closed aortic valve.

SUMMARY

The present disclosure relates to an implantable cardiomechanical sensor that is capable of measuring longitudinal, radial and torsional motion/deformation (e.g. strain and strain rate) in the heart. In some embodiments, these data can be used to improve cardiac resynchronization therapy timings for implantable cardiac stimulation devices and systems. For example, the time to peak strain in the septal and lateral regions of the myocardium can be compared to determine whether dysynchrony exists. If dysynchrony exists, interventricular timing and atrioventricular timing can be adjusted to reduce the level of dysynchrony. In other embodiments, the data can be used to detect a myocardial infarction.

In one aspect, the invention relates to an implantable cardiac stimulation device that includes a first lead adapted to be implanted in or on the heart of a patient. The first lead is adapted to provide therapeutic stimulation to the heart of the patient and includes a first mechanical sensor that obtains measurements indicative of the physical contraction and relaxation of the walls of the heart during systole and diastole. The device also includes a controller that induces a delivery of therapeutic stimulation to the heart of the patient via the first lead. The controller receives signals from the first mechanical sensor indicative of the contraction and relaxation of the walls of the heart; develops a template signal that corresponds to the observed contraction and relaxation of the walls of the heart during systole and diastole; and uses the template signal to modify the delivery of therapeutic stimulations being provided to the heart so that the heart's function during systole and diastole is improved.

In another aspect, the invention relates to an implantable assessment device that includes a controller configured to accept inputs related to cardiomechanical strain of a lateral region of a left ventricle of a heart and cardiomechanical strain of an interventricular septal region of the heart. The controller computes an interventricular dysynchrony index based upon the cardiomechanical strain input from the lateral region of a left ventricle of a heart. The controller may also determine the times of peak cardiomechanical strain from the inputs.

In yet another aspect, the invention relates to a method for assessing myocardial function using cardiomechanical sensors. The method involves acquiring data over a period of time from a first implanted myocardial mechanical sensor and a second implanted myocardial mechanical sensor separated by a distance; summating the acquired data from the first and second implanted myocardial mechanical sensors; and taking a derivative of the summated acquired data over the period of time to determine a first strain rate index.

In yet another aspect, the invention relates to an implantable cardiomechanical assessment system that includes an implantable cardiomechanical sensor system comprising at least a first myocardial mechanical sensor and a second myocardial mechanical sensor. The system also includes an implantable controller system coupled to the implantable cardiomechanical sensor system that is configured to acquire data over a period of time from the first implanted myocardial mechanical sensor and the second implanted myocardial mechanical sensor, summate the acquired data and calculate a derivative of the summated acquired data to determine a first strain rate index.

BRIEF DESCRIPTION OF THE DRAWINGS

Further features and advantages of the present disclosure may be more readily understood by reference to the following description, taken in conjunction with the accompanying drawings, in which:

FIG. 3A is a micrograph of a segment of myocardium. FIGS. 3B and 3C are schematic representations of muscle undergoing lengthening and shortening, respectively.

FIG. 4 shows graphs of myocardium tissue velocity and displacement derived from tissue tracking echocardiogram data.

FIG. 5B shows velocity, displacement, strain rate and strain curves for myocardial tissue at the apex, mid-wall and base of the heart.

FIG. 10B is a diagram of two CMESs, one disposed in the apical region of the heart and the other in the basal region of the heart, being used to detect torsional deformation of the heart.

FIG. 10C is a schematic of two CMES lead configurations, one with CMES material deposited in strips parallel to the lead axis and the other with CMES material deposited in a helical configuration around the lead.

FIG. 10D shows a graph of cardiac translation and expansion and a graph of cardiac rotation.

DETAILED DESCRIPTION

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
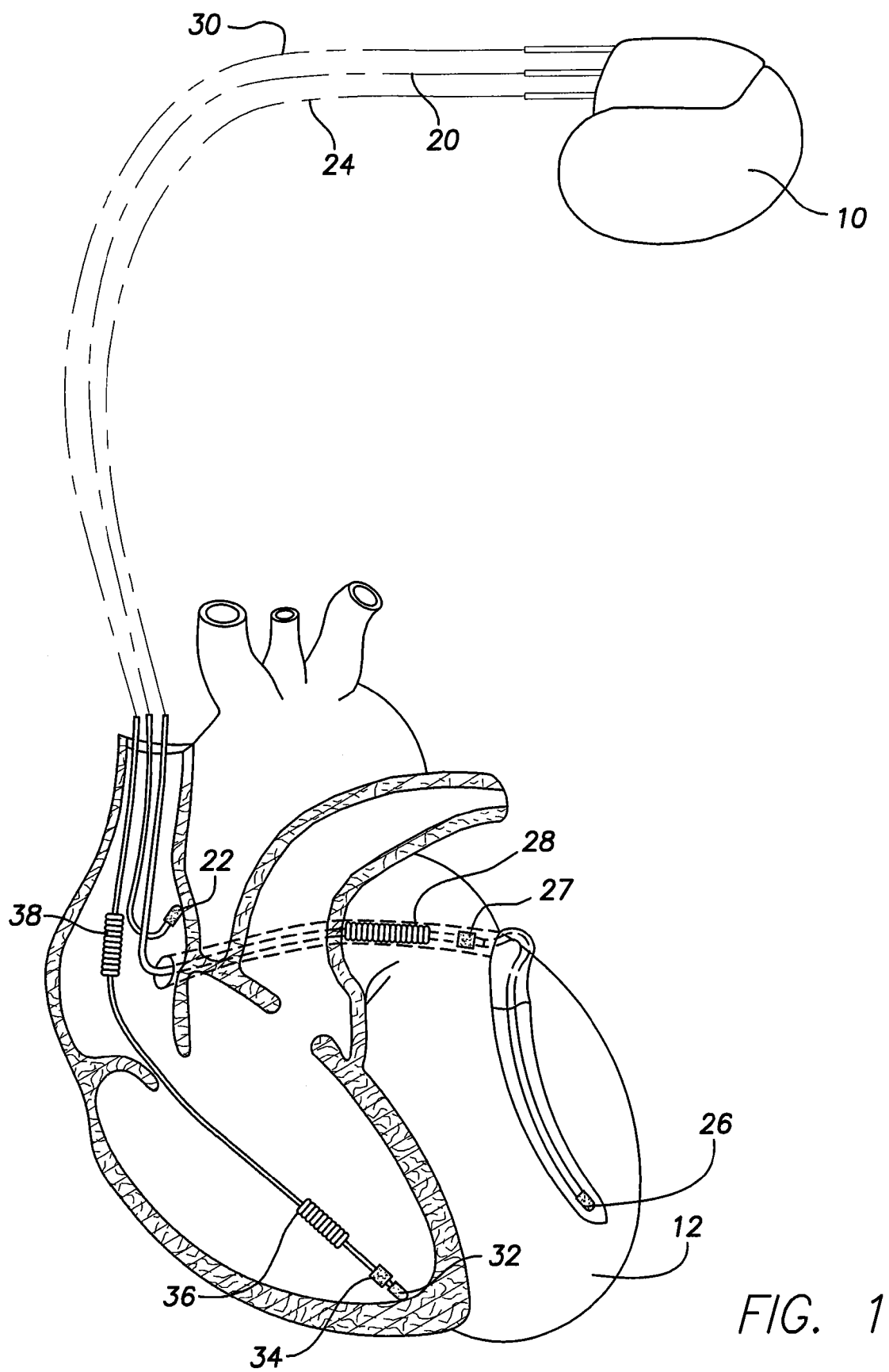
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The right atrial lead 20, the coronary sinus lead 24, and the right ventricular lead 30 can all incorporate cardiomechanical electric sensor (CMES) material so that the leads can function to provide cardiac mechanical motion data as described herein.

Figure 2A:
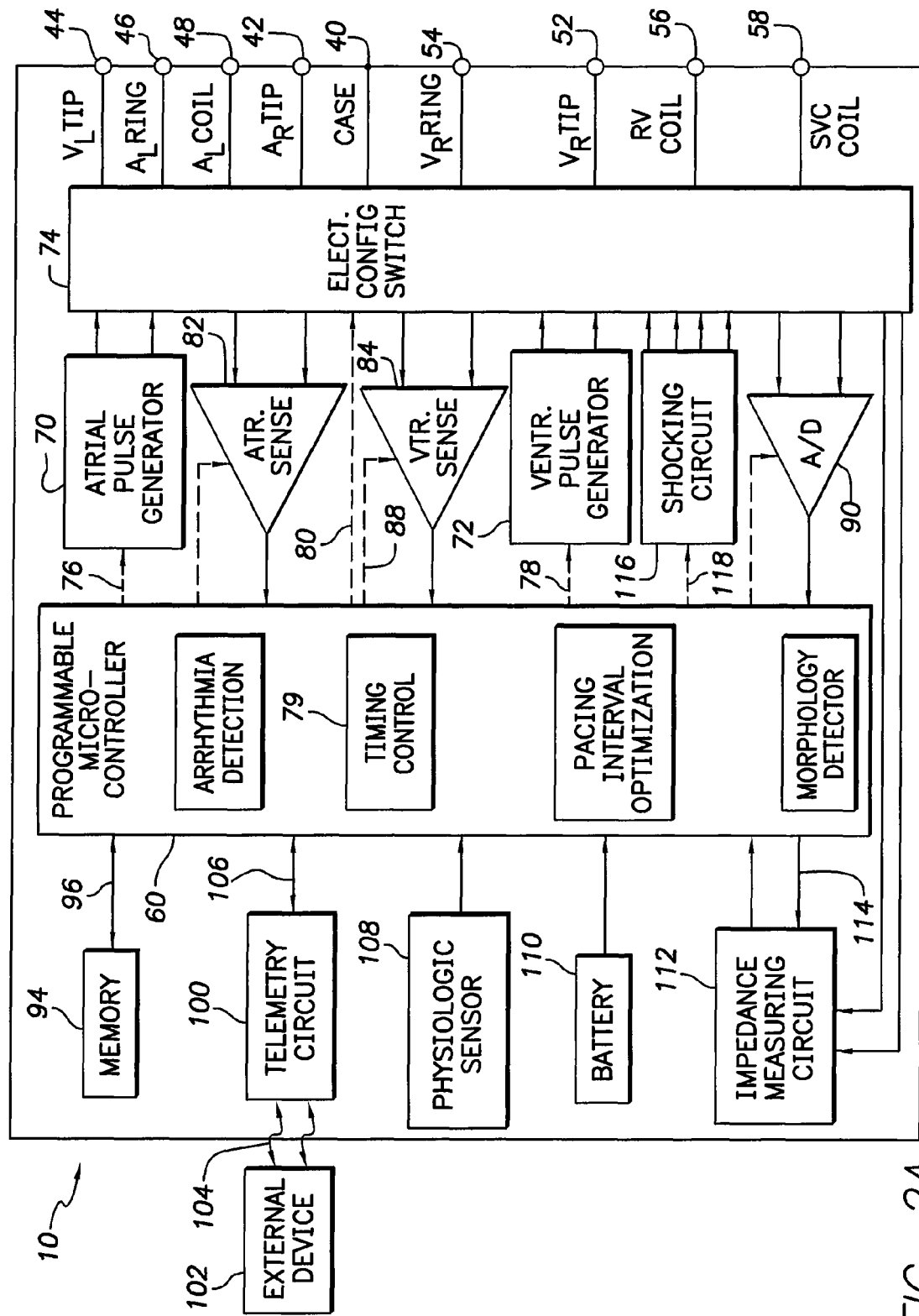
FIG. 2A is a functional block diagram of a multi-chamber implantable stimulation device illustrating the basic elements of a stimulation device which can provide cardioversion, defibrillation and pacing stimulation in four chambers of the heart.

As illustrated in FIG. 2A, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2A, is often referred to as the "can", "case" or "case electrode" and may be programmably selected to act as the return electrode for all pacemaker "unipolar" modes. The housing 40 may further be used as a return electrode alone or in combination with one or more of the coil electrodes, 28, 36 and 38, for shocking purposes. The housing 40 further includes a connector (not shown) having a plurality of terminals 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2A, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit 82, 84 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits 82, 84 are connected to the microcontroller 60 which, in turn, are able to trigger or inhibit the atrial and ventricular pulse generators 70, 72 respectively, in a demand fashion in response to the absence or presence of cardiac activity in the appropriate chambers of the heart.

For arrhythmia detection, the device 10 utilizes the atrial and ventricular sensing circuits 82, 84 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators 70, 72 generate stimulation pulses.

The stimulation device additionally includes a battery 110 which provides operating power to all of the circuits shown in FIG. 2A. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monofluoride or a hybrid of the two.

As further shown in FIG. 2A, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the LA coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the LA coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

A variety of diseases such as cardiomyopathy, congestive heart failure, hypertrophic cardiomyopathy, aortic stenosis and ischemic heart disease show characteristic abnormalities in myocardial strain, myocardial tissue velocity and myocardial tissue displacement, rotation and torsion. Tissue Doppler imaging (TDI) data is used to derive myocardial strain and strain rate by analysis of regional disparities in tissue velocity or the spatial location of ultrasonic reflectors (speckle tracking) as a function of time. This information is used clinically to evaluate properties of myocardial motion and deformation that provide insight into the electromechanics of the heart.

In some embodiments, lead-based sensors may be used as an alternative to TDI for generating quantitative information which relates to the same properties such as myocardial strain, myocardial strain rate, myocardial tissue velocity and myocardial tissue displacement, rotation and torsion. Sensors capable of acquiring this data can be used for monitoring purposes and communicate information related to cardiac performance and dysynchrony to the clinician. The same data can be used as part of a closed loop system for CRT timing.

Piezoelectric materials will generate a voltage when subject to mechanical stress or strain, with the magnitude of voltage dependent upon the magnitude of the stress or strain. In some embodiments, sensors comprised of piezoelectric material and positioned in locations optimal for detection of cardiac deformation and/or motion generate raw signals of cardiac mechanical data that can be further processed into myocardial strain, myocardial strain rate, myocardial tissue velocity and myocardial tissue displacement, rotation and torsion data.

Figure 2B:
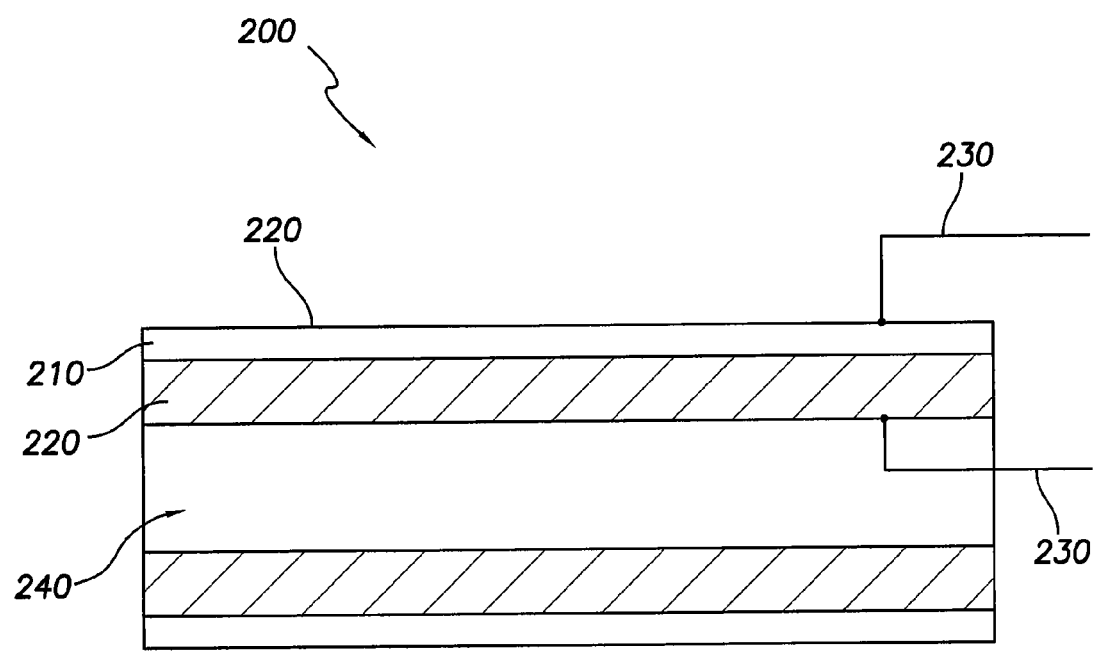
FIG. 2B illustrates a cross section of an embodiment of a cardiomechanical electric sensor.

Embodiments of CMESs may comprise one or more piezoelectric transducers, which convert mechanical motion into electrical signals. As illustrated in cross section in FIG. 2B, in some embodiments, a CMES 200 comprises a tubular and/or annular piezoelectric element 210, either self-supporting or disposed on a supporting structure. In some embodiments, conductors 220 contact the inner and outer surfaces of the tubular or annular element 210. Electrical connections 230 are coupled to the conductors 220.

In preferred embodiments, the sensor 200 is dimensioned for incorporation into a lead. For example, in some embodiments, the outer diameter of the sensor 200 is similar to the outer diameter of a lead, permitting the sensor to be disposed at any position along a lead without causing a profile change that could affect placement of the lead. In some embodiments, one or more of an electrode and/or other sensors is disposed over at least a portion of the sensor 200. A longitudinal passageway 240 through the sensor 200 in the illustrated embodiment permits routing electrical and/or other types of connections therethrough, for example, from one or more electrodes and/or sensors disposed on the same lead.

The conductors 220 comprise any suitable material known in the art, for example, titanium, titanium alloy, titanium nitride, platinum, platinum alloy, carbon, niobium, niobium alloy, tantalum, tantalum alloy, gold, combinations, and the like. In some embodiments, a patient's tissue is used as one of the conductors. In some embodiments, an elastomer is disposed over the sensor 200 (not illustrated). Preferred elastomers are biocompatible, including, for example, silicones, polyurethanes, ethylene-propylene copolymers, fluorinated elastomers, combinations, and the like.

In some embodiments, the piezoelectric element comprises a relatively hard material, thereby permitting reliable measurements with only small deflections of the piezoelectric material. Preferred piezoelectric materials are biocompatible, for example, ceramic piezoelectric materials, including ceramic ferroelectric particles, lead zirconate titanate (lead zirconium titanate, PZT), barium titanate, sodium potassium niobate, and the like. In some embodiments, the piezoelectric material comprises $Na_{0.5}K_{0.5}NbO_3$, for example, as described in U.S. Pat. No. 6,526,984. Other piezoelectric materials or deformation-based sensors may also be used.

One preferred sensor configuration comprises a piezoelectric material that is thin and covers a large amount of myocardial tissue surface area. Covering a large surface area provides global deformation data in comparison to the local information acquired by CMES material deposited in a smaller region. In order for data to be representative of myocardial deformation the CMES preferably contacts myocardium, and thus, the CMES is preferably located along the distal portion of a lead body and contours along either a large caliber coronary sinus lead or the epicardial surface if the CMES is deployed via a limited thoracotomy (e.g., a pericardial or epicardial approach).

In other embodiments, the CMES comprises a conductive polymer that has a resistance that changes as a function of strain. By measuring the resistance of the conductive polymer, the strain can be determined. The conductive polymer can be polyacetylene, polyaniline, polypyrrole or any other suitable conductive polymer.

In some embodiments that use piezoelectric materials, the raw CMES signal is a measurement of deformation (strain), and can be expressed in units of voltage. Referring to FIG. 3A, which depicts a micrograph of some isolated cardiac muscle fibers 304 from the heart, contraction and relaxation of the myocytes may be quantified by the deformation of adjacent mechanical sensors. Strain in the myocardium may be measured by the change in relevant length of myocardium:

$$\text{Strain} = e = (L - Lo)/Lo \tag{Eq. 1}$$

The strain (e) given by Eq. 1 is a dimensionless quantity. Strain is measure of a fractional change from unstressed dimension given by the unstressed zero length. Referring to FIGS. 3B and 3C, an expansion to the muscle fiber 304 length L 302 from the initial length Lo 300 represents a positive strain, while a compression and dimensional shortening represents a negative strain L 302.

A first order derivative of the raw strain signal with respect to time generates a measure of the deformation (strain) rate. The calculated quantity, strain rate, with the unit 1/s is a measure of the rate of deformation and is equivalent to the shortening or lengthening velocity per fiber length.

The microcontroller 60 can also comprise circuitry to process data obtained by the CMES as described herein as part of a closed loop system. Alternatively, the data obtained by the CMES can be communicated to an external device 102 and processed thereafter.

Derivation of CMES Derived Deformation and Velocity Indices

FIG. 4 depicts a velocity curve 400 of a region of the myocardium 402 generated by tissue tracking data derived from echocardiographs 404. Tissue tracking images are two-dimensional maps that display color-coded tissue velocity information and can be used to identify wall motion abnormalities and to estimate regional strain or shortening of the myocardium. Tissue tracking may be particularly useful in identifying wall motion abnormalities that may be treated with resynchronization therapy or may be used to optimize resynchronization therapy. A time of integral of the velocity curve 400 yields a displacement curve 406 of the same region of myocardium.

Figure 5A:
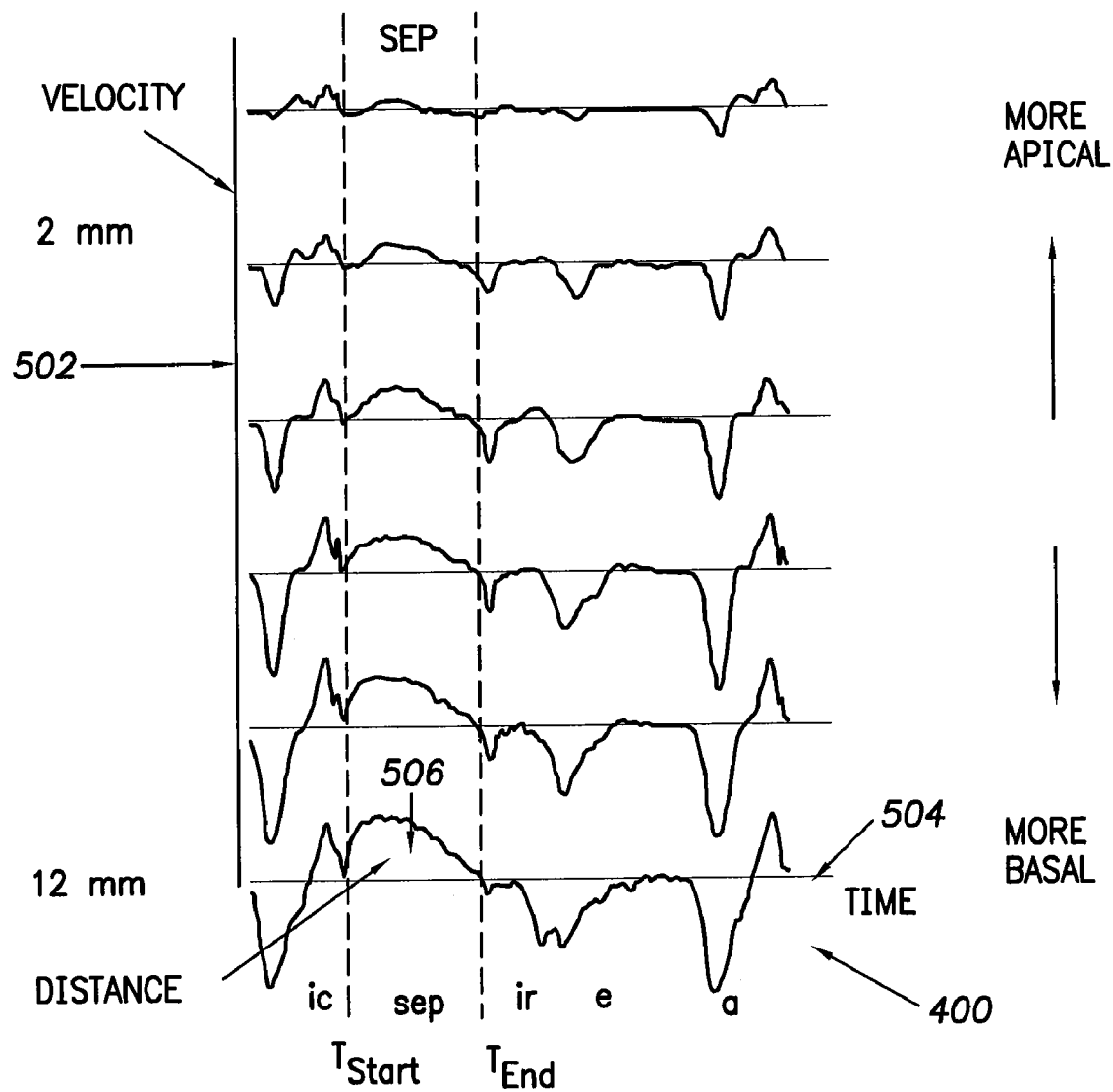
FIG. 5A shows tissue velocity curves for normal heart tissue segments from the apical region of the heart to the basal region of the heart.

FIG. 5A depicts echo-generated tissue velocity curves 400 in the apical to basal regions of the heart. The y-axis 502 represents the velocity, the x-axis 504 represents time and the area under the curve 506, which can be obtained by integrating the velocity curve 400, represents tissue displacement. FIG. 5B shows a velocity curve 400, a displacement curve 406 which can be obtained by integrating the velocity curve 400, a strain rate curve 510 and a strain curve 512 which can be obtained by integrating the strain rate curve 510 in the apex 514, mid-wall 516 and base 518 of the heart.

As shown in FIGS. 5A, and 5B, along a longitudinal axis generally parallel to the spine, the heart contracts and moves from base to apex during systole. The heart relaxes and moves in the opposite direction, from apex to base, during diastole. The basal regions generally move a greater distance, an average of approximately 12 mm at most basal segments, than the apical regions, which move approximately 0-2 mm at cardiac apex. A measurement of the relative difference in distance that any two regions traverse will generate longitudinal deformation (strain) information. Echocardiographic techniques such as tissue tracking demonstrate this displacement phenomenon as well as characteristics of velocity, strain and strain rate.

Figure 6:
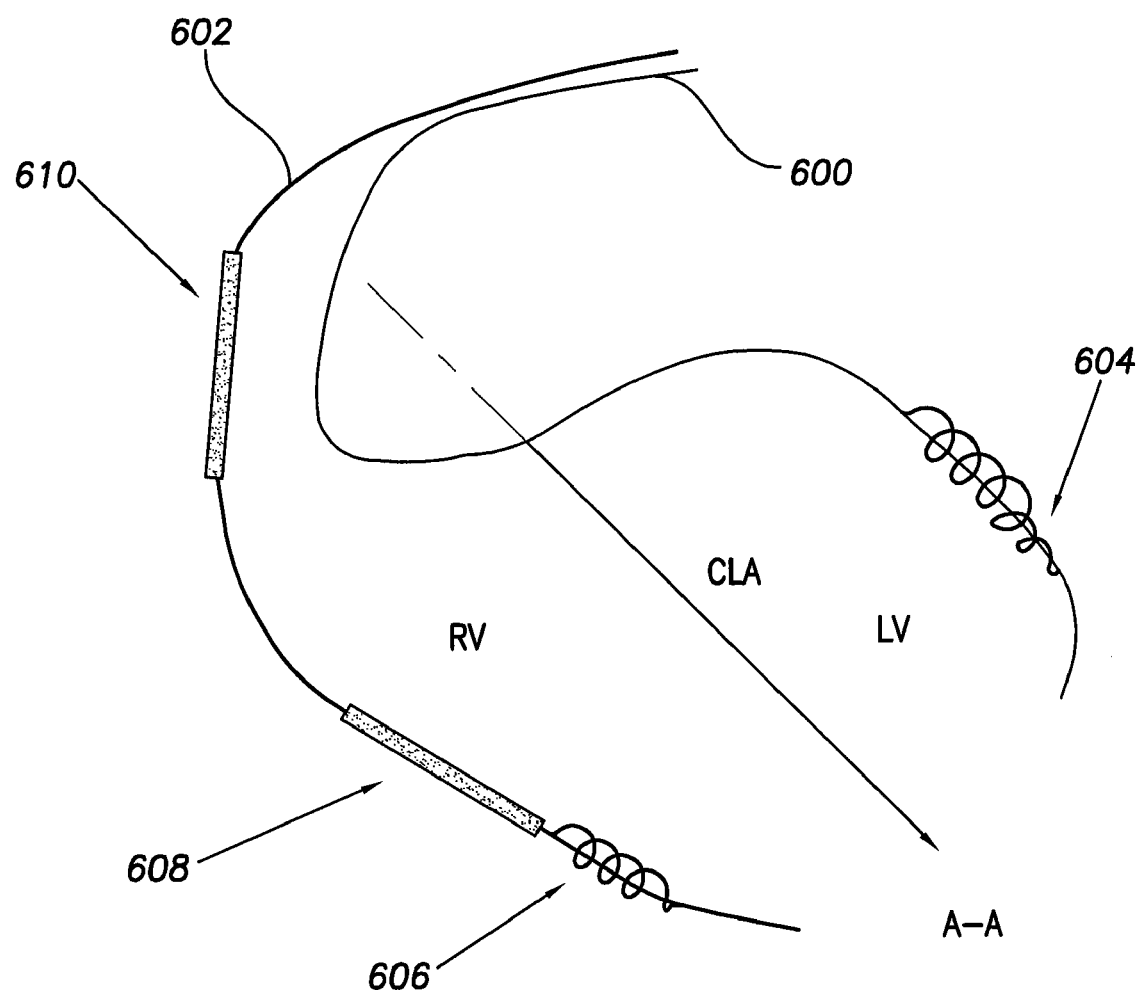
FIG. 6 is a schematic illustration of two leads, one disposed relative to the left ventricle and the other disposed relative to the right ventricle, each including a cardiomechanical electric sensor (CMES) for sensing one or more of myocardial motion and deformation.

In some embodiments, as shown in FIG. 6, a CMES-bearing device 600, such as an LV lead, is positioned with respect to the left ventricle (LV) such that a portion of the lead incorporating CMES material 604 is substantially parallel to the cardiac central longitudinal axis (CLA) to thereby acquire longitudinal deformation information. Similar information can be acquired by positioning another CMES-bearing device 602, such as an RV lead, such that a portion of the lead incorporating CMES material 606 is substantially parallel with the CLA. Both CMES devices 600, 602 generate data related to the motion of the cardiac apex relative to the base if the CMES material 604, 606 covers enough surface area along the CLA of the heart and contacts myocardial tissue. The greater the distance (base to apex) the CMES material 604, 606 traverses, the greater the amount of resultant deformation and the more global the representation of cardiac motion will be. In the case of the RV lead 602, additional CMESs 608, 610 may be included. Basally located CMES 610 will deform more than apically located CMES 608 and thus be more sensitive to changes in global cardiac geometry.

In some embodiments, regional contractile information can be generated from CMES material that covers a short distance. In normal hearts or hearts with global decreases in contractility (strain, deformation) such a reduced surface area electrode can provide information about global cardiac contractile function because any regional properties are homogeneous with global properties (e.g. dilated cardiomyopathy). However, in more anisotropic conditions, whether in the space domain or time domain, such as ischemic cardiomyopathy or electromechanical dysynchrony, respectively, regional information provides little information about global cardiac contractile function. As the heart is embryologically and structurally derived from a single muscle band that has certain deformation properties, tethering effects (e.g. regional myocardial shortening has a pulling effect on surrounding myocardium) create some degree of interrelation between regional and global cardiac deformation. Thus, CMES acquired data in the longitudinal axis will provide clinically relevant information if the material covers enough surface area (e.g. longitudinal lead length).

Relative differences in tissue velocity can be used to determine myocardial strain rate derived by using the strain rate equation. This technique is implemented in sophisticated echocardiography machines that are capable of tissue Doppler imaging for quantifying regional myocardial strain rate, strain, velocity and displacement. This equation can be similarly applied herein to derive analogous indices descriptive of the same myocardial properties using implanted CMES technology. The strain rate (SR) equation is:

$$SR = (Vb - Va)/x \tag{Eq. 2}$$

where Vb and Va represent regional velocities at points b and a, respectively, SR=strain rate and x=length between points a and b. The calculated strain rate is representative of the myocardial deformation in the region encompassing points a and b where the tissue velocities were measured. Similarly, Eq. 2 can be utilized to derive estimated tissue velocity information of cardiac motion by using the strain rate between points a and b measured with a CMES sensor capable of measuring strain. Taking the derivative of the strain with respect to time yields the strain rate, which can then be used in Eq. 2 to determine velocity information.

Figure 7:
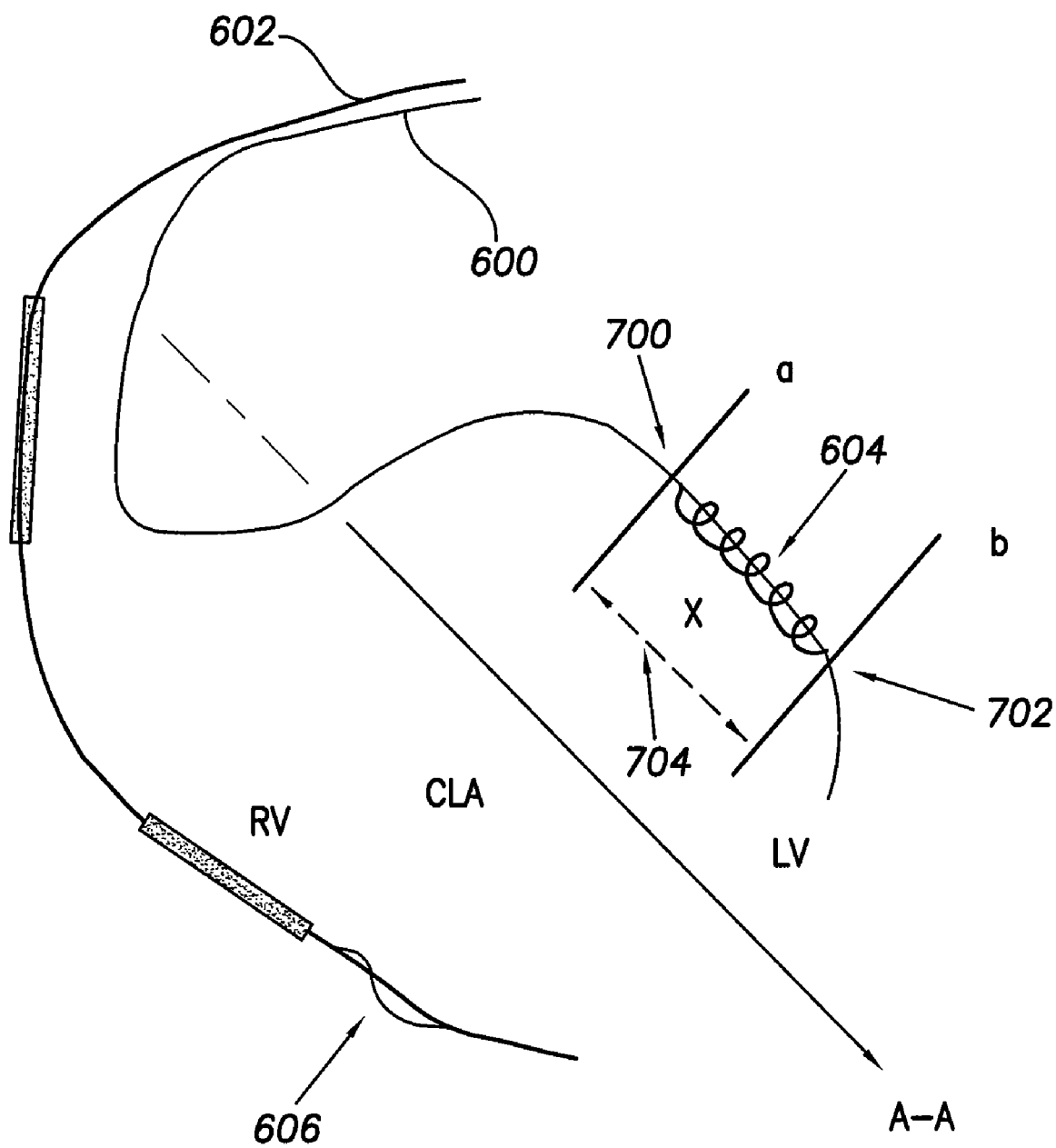
FIG. 7 is another schematic of the leads of FIG. 6 further depicting features related to myocardial velocity calculation.

For example in some embodiments, as shown in FIG. 7, if CMES material 604 in series and in contact with the myocardium at points a 700 and b 702, which are separated by distance x 704, the resultant summed deformation voltage Vsum that is generated by the series sensor material 604 provides strain information produced along distance x 704 and can be used to derive a deformation index. This property may also be acquired by depositing CMES material 604 along a relatively long portion of an implanted lead in contact with myocardium. In some embodiments, distance x 704 is in a range of about 4 mm to about 30 mm, preferably about 5 mm to about 20 mm, and most preferably about 5 mm to about 10 mm.

The first derivative of the signal generated from CMES deformation between points a and b as a function of time, dVsum/dt=dCMES/dt, is proportionate to SR and can be used to derive a SR index that can be plotted as a function of time. The integration of the SR index can be performed to derive an index of strain, which in some embodiments is an index of longitudinal strain. The measure of strain or strain rate between points a and b can be used to detect a myocardial infarct by comparing the measured strain or strain rate values with expected or normal strain or strain rate values. Abnormally low strain or strain rate values may indicate the presence of a myocardial infarct.

$$dCMES/dt = SR \text{ Index} \tag{Eq. 3}$$

In order to derive regional velocity information, a velocity index, Vi, can be defined that is representative of the spatial velocity gradient between points a and b, having a distance x, where Vb and Va represent regional velocities at points b and a, respectively. Rearranging Eq. 2, the strain rate equation, and substituting Vi for Vb−Va yields:

$$Vi = Vb - Va = (SR \text{ Index})*(x) \tag{Eq. 4}$$

Thus, by combining Eq. 3 and Eq. 4, the CMES derived Velocity Index, Vi, equals the first order derivative, d(CMES)/dt, multiplied by x, where x is the span of the distance between CMES electrodes a and b (or length along a lengthy CMES electrode). This index can be expressed in units, Voltage-cm/sec.

$$CMES \text{ Velocity Index} = d(CMES)/dt * x \tag{Eq. 5}$$

This index can be measured instantaneously by using d(CMES)/dt max or measured as a function of time during the cardiac cycle. This index generally parallels Tissue Doppler measurements of myocardial velocity. Integration of this velocity waveform will provide displacement information and measurements such as peak longitudinal displacement can be derived.

An alternate means of deriving an index of myocardial velocity is by defining the pure CMES signal as a measurement of motion (e.g. velocity, acceleration). In order for the CMES to represent motion rather than deformation, the CMES is preferably not fixated to myocardium and is instead relatively free floating.

Dysynchrony Index

Figures 8A, 8B:
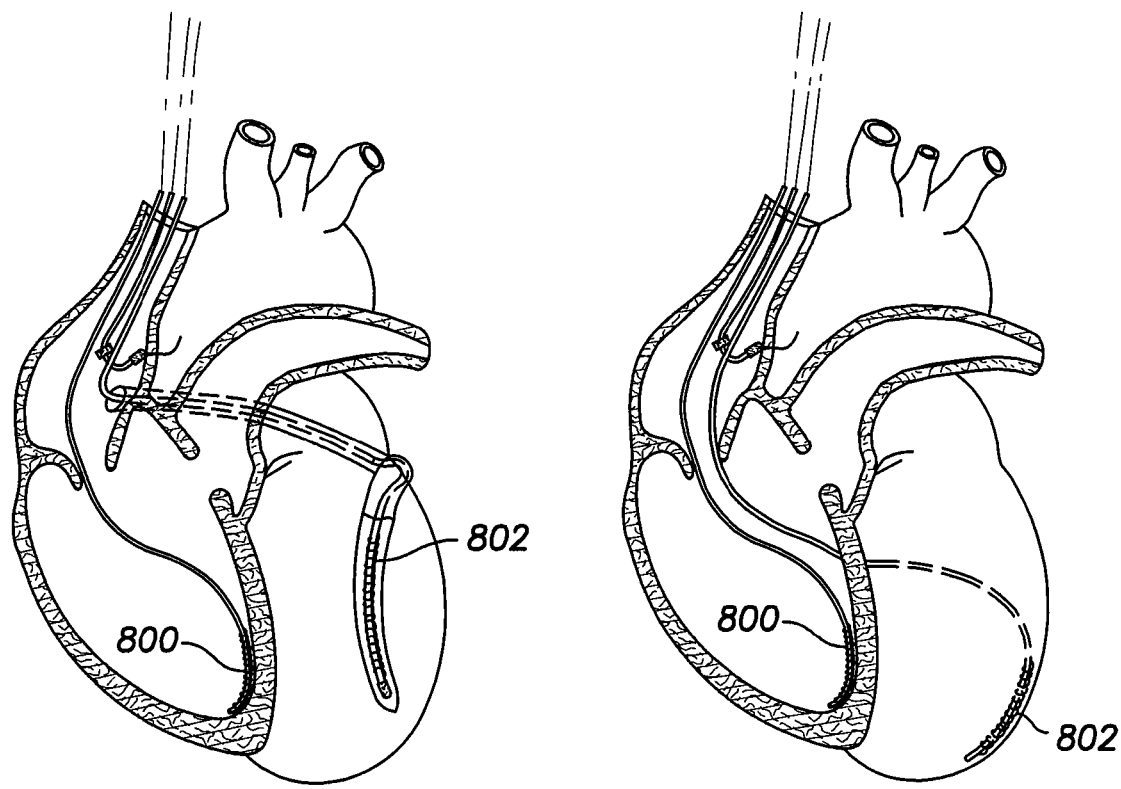
FIG. 8A shows two CMESs, one disposed in the interventricular septal region of the heart and the other in the coronary sinus region of the heart, being used to detect ventricular dysynchrony.
FIG. 8B shows two CMESs, one disposed in the interventricular septal region of the heart and the other in the lateral region of the left ventricle of the heart, being used to detect ventricular dysynchrony.
Figure 8C:
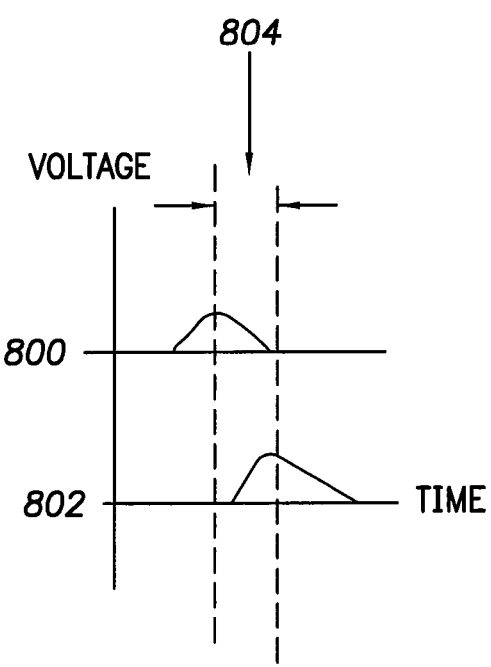
FIG. 8C are schematic voltage graphs from the two CMES electrodes.

In some embodiments, as shown in FIGS. 8A and 8B, if two or more CMESs 800, 802 are deployed in interventricular septal and LV lateral regions, respectively, information about dysynchrony can be derived. One CMES 802 can be deployed in the LV lateral region via the coronary sinus region (FIG. 8A) or by a transeptal approach (FIG. 8B). Alternatively, a pericardial approach (not shown) may be used to place the CMES 802 in the LV lateral region. Though electromechanical dysynchrony is an anisotropic property, differences between septal and lateral wall motion are often seen in patients suffering from dysynchrony and such measurements are considered specific indicators of patients who respond to cardiac resynchronization therapy (CRT) device implants. Thus, as shown in FIG. 8C, time of peak CMES Voltage (tCMESpeak) from the septal sensor 800 and lateral sensor 802 located in the distal portion of lead and proximate to myocardium may be used together to provide a CMES Dysynchrony Index or other parameter that is indicative of the time to peak myocardial strain, which is a currently utilized ultrasonic measurement of dysynchrony. In another embodiment, RV apically placed leads may generate similar information if the CMES material deformation is congruent with septal deformation during the cardiac cycle.

$$CMES \text{ Dysynchrony Index} = \frac{(tCMESpeak \text{ septal})}{(tCMESpeak \text{ lateral})} \tag{Eq. 6}$$

Alternatively, time to peak d(CMES)/dt, which will parallel measurements of time to peak SR, can be used instead to calculate the CMES Dysynchrony Index.

Other features of the CMES signal can be used for timing (e.g. time of onset of CMES voltage waveform (Vcmes) or time to peak dVcmes/dt). Generally, the relative timings of the CMES generated signals in opposing regions of interest, for example myocardial wall segments, can be utilized for deriving a dysynchrony index.

Figure 9:
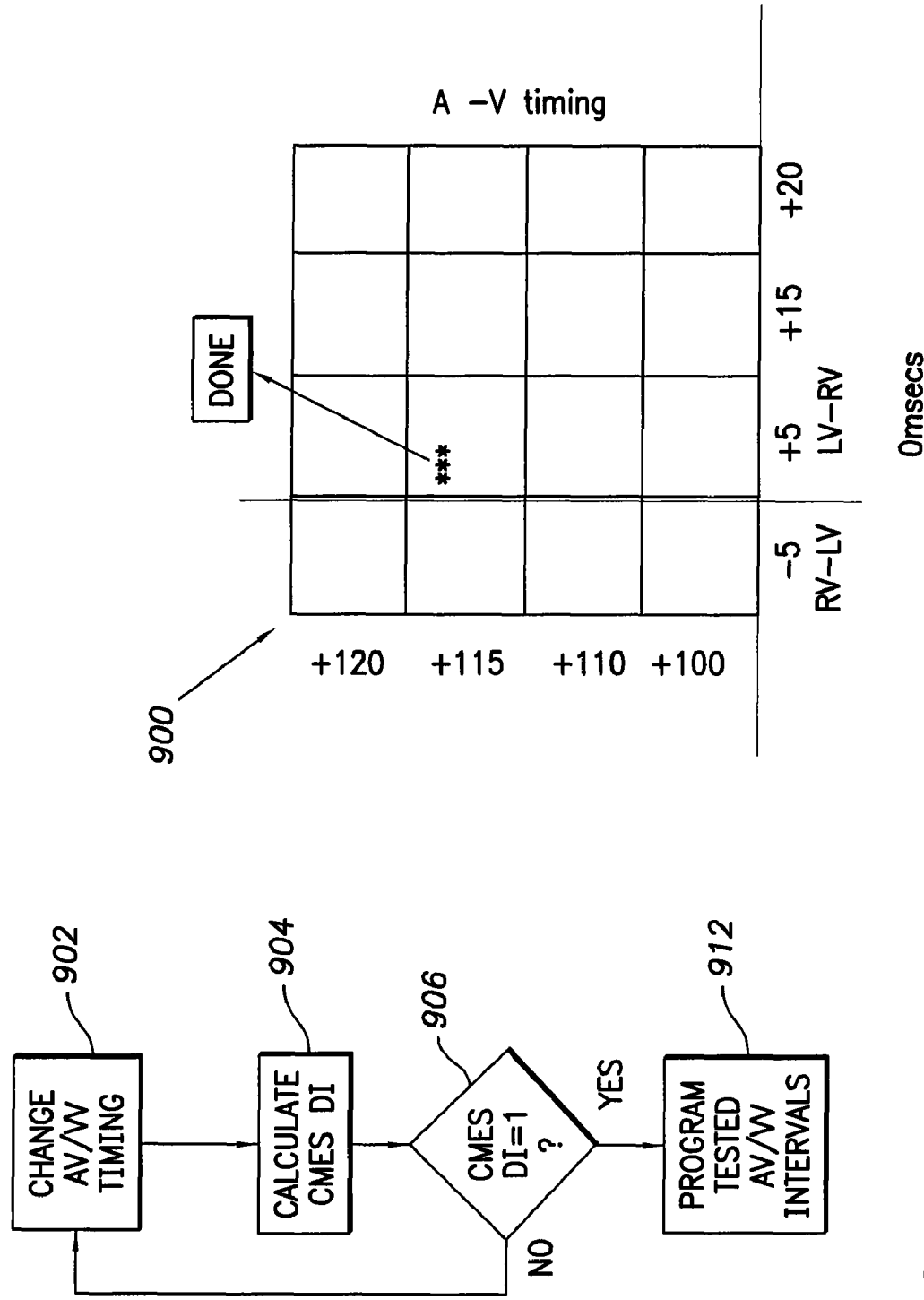
FIG. 9 depicts a block diagram for determining AV and VV timing settings that do not result in dysynchrony by using CMES and the Matrix Optimization Method.

As the CMES Dysynchrony Index approaches a value of one, conditions of synchrony will be present. Ideally, this time will occur during the latter portion of the systolic ejection phase, when strain 512 is maximal in normal hearts, as shown in FIG. 5B. As changes in interval timing occur, the index may be followed and the programmed intervals that yield an index that is closest to unity will be optimal. Changes in atrioventricular (AV) and interventricular (VV) timing can be made such that multiple permutations of AV and VV intervals are evaluated because changes in AV timing and VV timing do not have mutually exclusive effects on cardiac synchrony or systolic or diastolic performance. As shown in FIG. 9, an array or matrix 900 of several AV and VV intervals can be tested using a Matrix Optimization Method (MOM) while the CMES Dysynchrony Index (CMES DI) is evaluated for each permutation. MOM is described in greater detail in U.S. Pat. No. 7,010,347, herein incorporated by reference in its entirety. Regarding CMES DI evaluation, at block 904 CMES DI is calculated for a set of current AV and VV intervals. At block 906 the calculated CMES DI is compared to unity plus or minus a default value (e.g. a programmable standard deviation). If the CMES DI does not equal unity plus or minus the default value, the process returns to block 902 where another set of AV and VV intervals are selected and block 904 where another CMES DI is calculated. Once CMES DI equals unity plus or minus a default value, the tested AV and VV intervals are programmed into the device at block 912. The standard deviation can be derived by analysis of previous values during earlier optimization efforts.

The CMES Dysynchrony Index may also be used with intracardiac electrogram (IEGM) data for monitoring electromechanical dysynchrony in the heart. If electromechanical dysynchrony is detected, lead based CMES electrodes, as described herein, can be used to implement resynchronization timing therapy as part of a closed loop system. See, for example, U.S. Pat. No. 7,010,347, previously incorporated by reference.

Radial Deformation and Cardiac Rotation

Figure 10A:
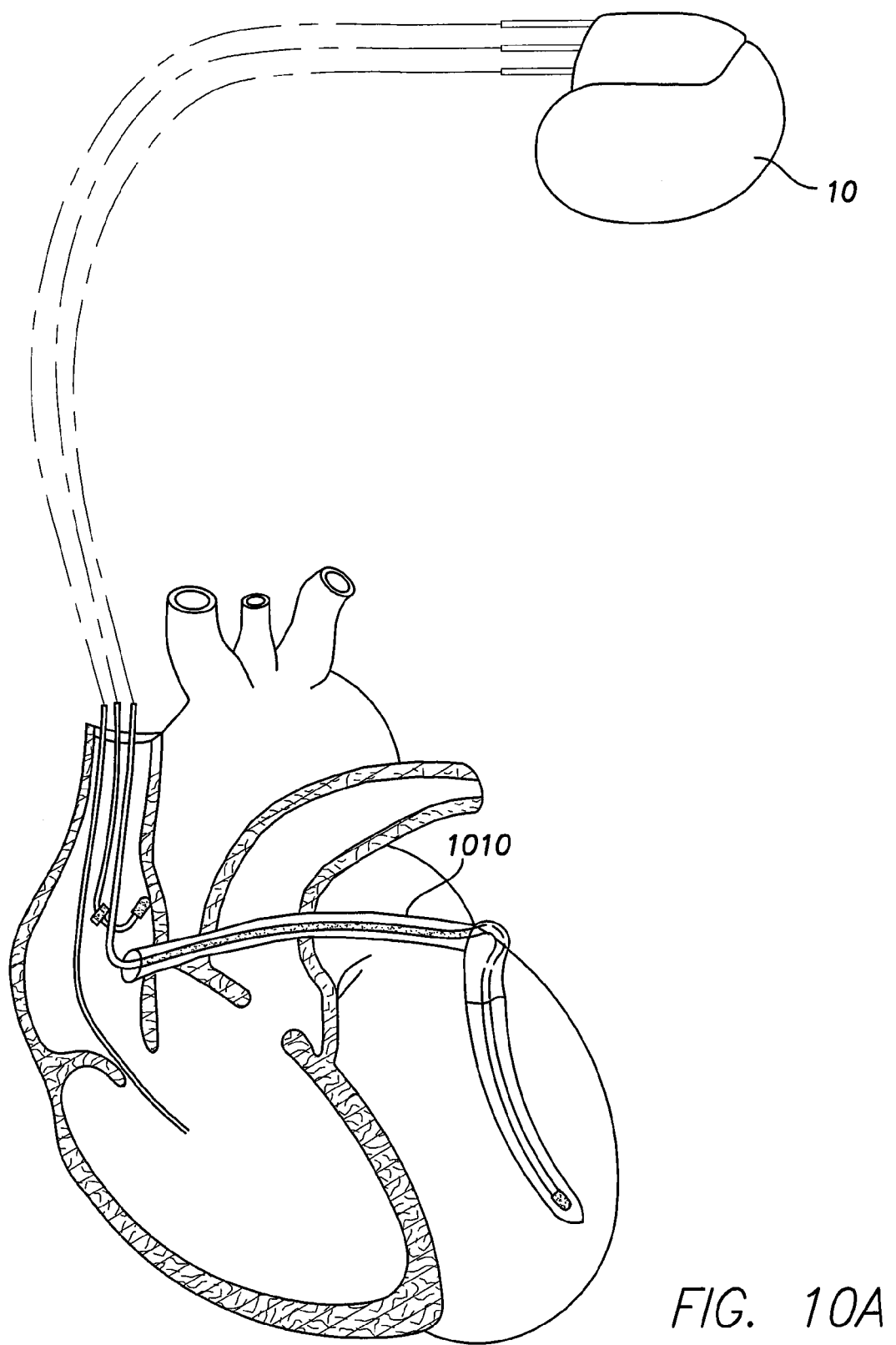
FIG. 10A is a diagram of one CMES disposed in the coronary sinus region of the heart, being used to detect radial deformation and rotation of the heart.

With reference to FIGS. 10A and 10B, in some embodiments, CMESs 1010 may be deployed circumferentially along the proximal to lateral portion of the main coronary sinus branch (endovascular leads) (FIG. 10A), or along the AV groove (pericardial leads) (FIG. 10B). In these arrangements, parameters of radial deformation and motion can be derived. Radial strain can be used as a global cardiac performance index. However, radial strain is subject to regional effects and the performance of more apical segments may not be well represented, leading to the possibility that regional pathology (e.g. an mid-cavitary or apical infarct) will not be detected.

In some embodiments, a lead configuration where the CMES is in close proximity to tissue and not free-floating may be utilized to derive rotational velocity information using Eq. 5, thereby providing an index of basal cardiac rotational velocity. If this data is also acquired about the cardiac apex, which is preferably obtained with a pericardial or epicardial lead deployed using a sub-xyphoid approach as shown in FIG. 10B, relative rotational data can be acquired for derivation of a torsion index. In normal hearts, the cardiac base rotates in an opposite direction from the apex. For example, during isovolumic contraction, the base rotates counter-clockwise while the apex rotates clockwise. The opposite motion occurs during isovolumic relaxation as shown in FIG. 10D. In FIG. 10D, curve 1000 represents tissue velocity as a function of time for basilar systolic counter-clockwise rotation and diastolic counter-clockwise rotation. Curve 1002 is apical systolic clockwise rotation and diastolic counter-clockwise rotation. This torsion effect is pivotal in generating forces that contribute to isovolumic contraction, aortic valve opening and systolic forward flow and a diastolic suction effect that contributes to early diastolic rapid filling during isovolumic relaxation. Time T 1004 is diastolic filling time where no torsion is present and the heart translates and expands 1006 rather than rotates. Identification of this timeframe using intracardiac electrograms (e.g. just before and after the P wave) can assist in temporal labeling of the generated CMES signals (see below). Leads placed using a pericardial or epicardial approach are generally more appropriately oriented for generation of clinically relevant CMES signals.

In some embodiments, circumferential deformation effects (i.e. systolic circumferential shortening) will contribute to the raw radial CMES signal data. Thus, the derived rotational velocity information includes both the actual rotational velocity information plus a contribution from circumferential deformation effects. In studies using Tissue Velocity Imaging, the estimated amount of contribution of circumferential deformation to the measured velocity data is approximately 13% in normal patients and under 5% in patients with Class III or IV heart failure and ejection fraction less than 40% (personal, unpublished data). Thus, application of Eq. 5 to radially derived CMES data will provide a relatively accurate index of pure cardiac rotational velocity with some contribution from the effects of circumferential deformation. The amount of contribution of circumferential deformation and of rotational velocity to the data acquired will also relate to the amount of contact the sensor has with underlying tissue. Nonetheless, this cardiac performance index is a useful blend of rotational velocity and circumferential contractile properties. If directional information can be derived (e.g. clockwise vs. counter-clockwise) from sensors 1010 and 1012 positioned in the apex and base, respectively, as shown in FIG. 10B, a torsion index can be obtained by adding the measured indices (in essence adding the absolute values as the rotational vectors are opposite). Patients with more advanced heart failure will have less rotation and/or torsion and less circumferential deformation with a resultant translational motion without significant rotational velocities. Thus, the resulting CMES rotational and torsional index will be less in these patients. Integration of rotational or torsional dCMES/dt will derive a rotational or torsional displacement index, respectively.

Inferred Polarity

In some embodiments, embedding CMES material on an implantable lead such that the voltage generated relies on the direction of deformation will allow the derivation of more accurate representations of actual physiologic properties. For example, as shown in FIG. 10C, the CMES material 1014 can be placed in strips parallel 1016 to the long axis of a lead body 1018 or in a helical fashion 1020 about the lead body 1018. If a lead placed about the AV ring (basal location) has CMES material embedded parallel to the lead long axis, the raw voltage signal generated is more of a function of radial deformation. If the CMES material runs in a helical fashion about the long axis of the lead, the raw voltage signal generated is more a function of circumferential deformation.

In some embodiments, if basal and apical CMES electrodes 1010 and 1012 are designed to derive rotational indices as shown in FIG. 10B, certain assumptions about direction of deformation may be made. For example, if deformation of the CMES material causes it to expand, a different voltage waveform will be generated than if the CMES material contracts. The waveform polarity will not be significantly different as the cardiac forces causing the deformation from the original length result in a voltage signal regardless of material contraction or expansion. Certain characteristics of the raw voltage signal (e.g. relative positive to negative polarity in a signal that is not rectified), however, will be seen as a result of CMES material contraction rather than expansion and vice versa. Signal processing can be applied to derive such polarity information.

Figure 11:
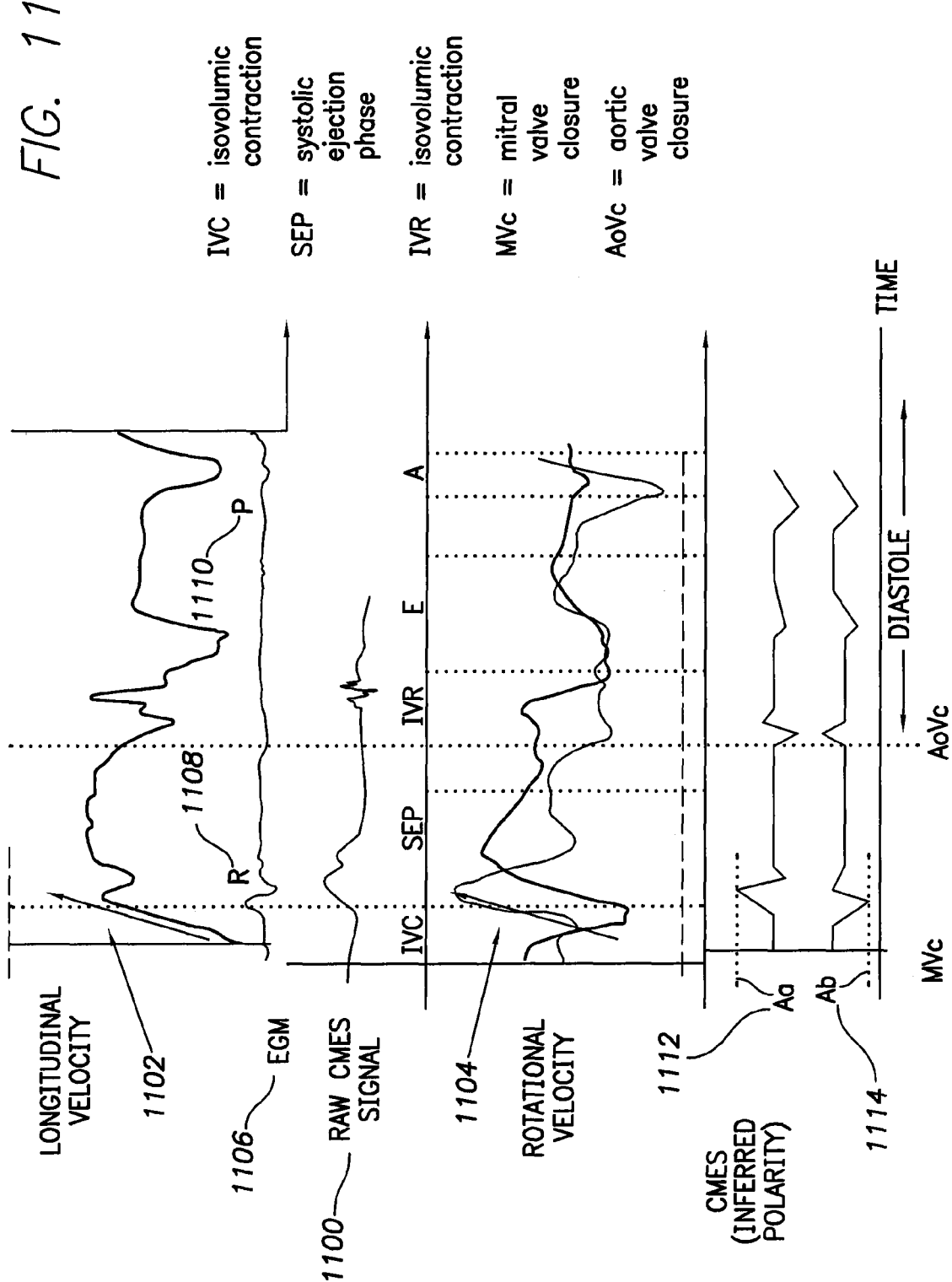
FIG. 11 shows how polarity of the CMES signal can be inferred from graphs of an EGM, the raw CMES signal, the longitudinal velocity and the rotational velocity.

Referring to FIG. 11, the timing of the voltage signal 1100 will relate to systolic (e.g. isovolumic contraction) and diastolic (e.g. isovolumic relaxation) deformation voltages, Vsys and Vdias, respectively. Isovolumic contraction (IVC) causes a steep rise in longitudinal myocardial tissue velocity 1102, rotational velocity 1104, longitudinal and radial deformation (strain). IVC typically occurs shortly after depolarization. Vsys will typically occur shortly after the electrocardiogram 1106 (EGM) R wave 1108, while Vdias will typically occur thereafter, before the EGM P wave 1110. In a normal heart, deformation of a lead-based CMES with specific lead orientation and material characteristics (e.g. parallel to lead body, parallel to the cardiac CLA) can be expected to be a result of longitudinal rather than radial deformation. Similarly, inferences about whether a voltage signal is generated as a result of longitudinal systolic contraction rather than diastolic expansion may be made. For example, systolic longitudinal contraction will occur during IVC. This will lead to contraction of CMES material positioned along the length of a lead that is parallel to the cardiac CLA. The resulting waveform will occur after the EGM R wave and thus, the second CMES voltage waveform, Vdias, can be inferred to be a result of material expansion during diastole. Likewise, the EGM R to Vsys interval will be shorter than the EGM R to Vdias interval, and the interval from Vdias to the next EGM R will be shorter than the interval from Vsys to the next EGM R. Furthermore, Vdias will often be of lower amplitude than Vsys as the forces generated from diastolic expansion (isovolumic relaxation, IVR) are of less amplitude and are generated more slowly than systolic contraction that occurs during IVC. Identification of the temporal relationship of these waveforms to the intracardiac P wave will assist in labeling a given signal as one generated from contraction and not relaxation. These temporal and morphologic signal characteristics will allow the system to infer polarity of deformation information. Apically located CMES sensors 1112 will have an assigned polarity that is different than basally located CMES sensors 1114 which is represented on bottom of FIG. 11 as Aa and Ab, respectively. Under normal circumstances these deflections (with inferred polarity) will be in the opposite direction as shown, though in patients with congestive heart failure the amplitude will be less and the direction of these signals may be similar (secondary to translation without rotation and impaired circumferential shortening).

In the pathologic heart, these temporal and morphologic signal characteristics may be less accurate and signal processing for determination of inferred polarity will be less reliable. This is due to the increased dissociation between the electrical and mechanical properties of abnormal myocardium. Because of this, material characteristics may be modified as to generate specific raw signal voltage waveforms that are more characteristically seen with contraction or expansion. With such CMES characteristics, signal processing to derive the inferred polarity can be simplified and the resulting information more accurate.

Figure 12:
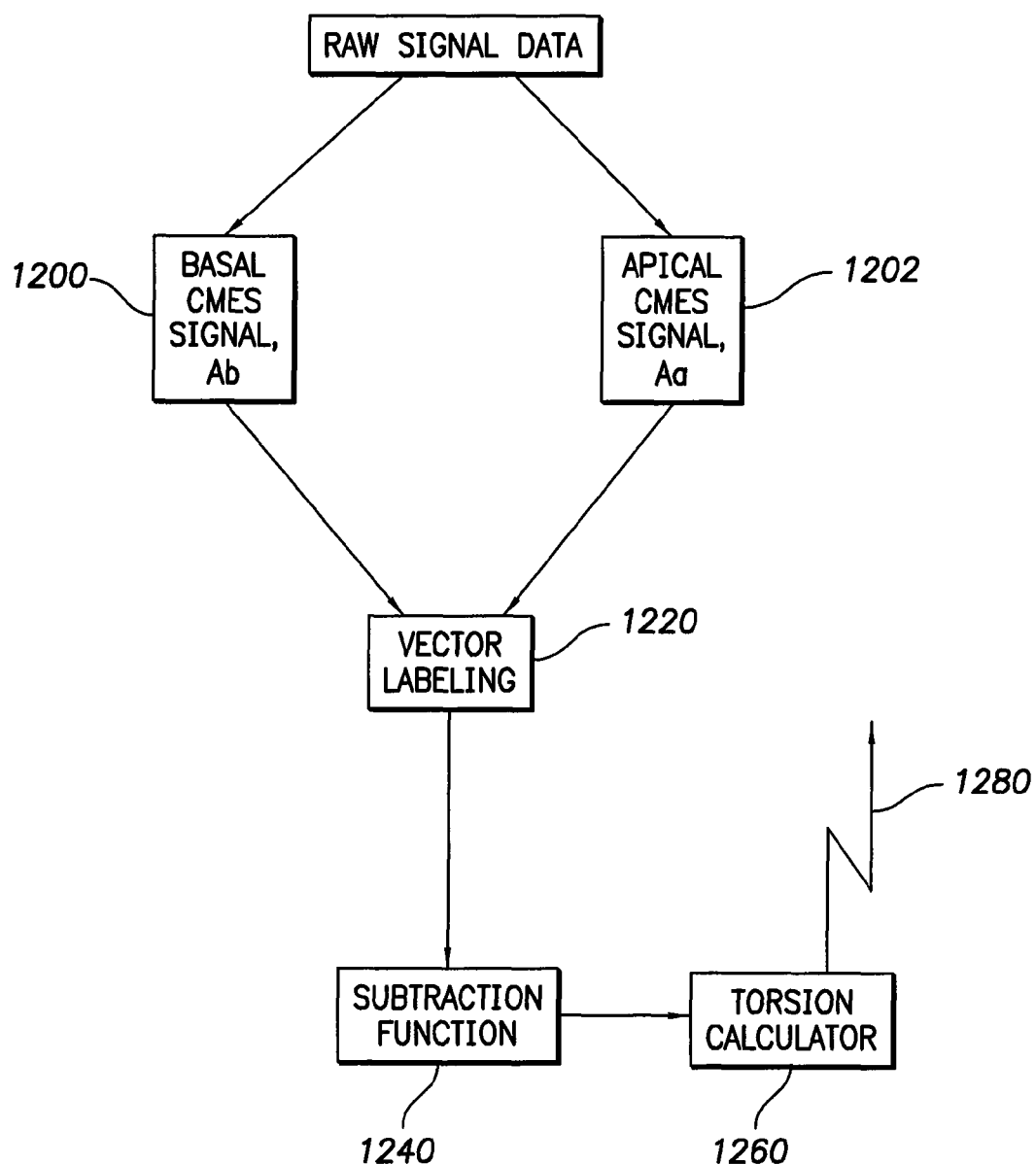
FIG. 12 is a block diagram for calculating the torsion of the heart.

In some embodiments as shown in FIG. 12, the apical and basal CMES signals are processed at blocks 1200, 1202. The processed signals are then vector labeled based on temporal and morphologic characteristics at block 1220. At block 1240, a subtraction function is utilized to calculate the difference in rotation between Aa 1112 and Ab 1114 (bottom of FIG. 11). The accuracy of the subtraction function is dependent upon appropriate vector labeling. At block 1260 a torsion calculator is optionally implemented to generate data in numerical format that is communicated 1280 from the device to the programmer via wireless telemetry. Alternatively, some of the processes shown in FIG. 12 can be performed within the programmer itself. In some embodiments, torsional velocity calculation is performed by analysis of relative values from basal and apical CMES sensors as described above. Derivation of a rotational displacement index can be performed by integration of the derived rotational velocity waveform.

It is noteworthy to mention that a combination of the forces generated during isovolumic contraction and relaxation will contribute to the development of the CMES signal and direction specific information may not always be able to be characterized. Thus, in some embodiments, CMES data can provide a crude representation of deformation and/or motion. The more myocardial surface area the CMES material covers, the more physiologically accurate the derived indices will be at characterizing the mechanical events occurring during isovolumic contraction and relaxation. It is also noteworthy to mention that the temporal characteristics of the raw CMES voltage signal occur on or about the time of mitral valve and aortic valve closure, but are only temporally related to these events rather than representative of valvular mechanics. Under circumstances where the CMES sensor is free floating, myocardial acceleration (and possibly dP/dt, the rate of change in blood pressure at the sensor site) and acoustical information may be derived.

Any and all of the data described herein can be used for monitoring cardiac performance and properties of dyssynchrony. Likewise, the same data can be implemented for optimization of interval timing for any multi-site pacing system in a closed loop fashion as depicted in FIG. 9 which describes the Matrix Optimization Method.

In an alternate embodiment, periodic interval monitoring is used to derive any of the indices described herein. During time frames where diagnostic data is not collected, the voltage generated from the CMESs is stored as energy to reduce the costs to the system (e.g. battery longevity) of operating such software.

Figure 13:
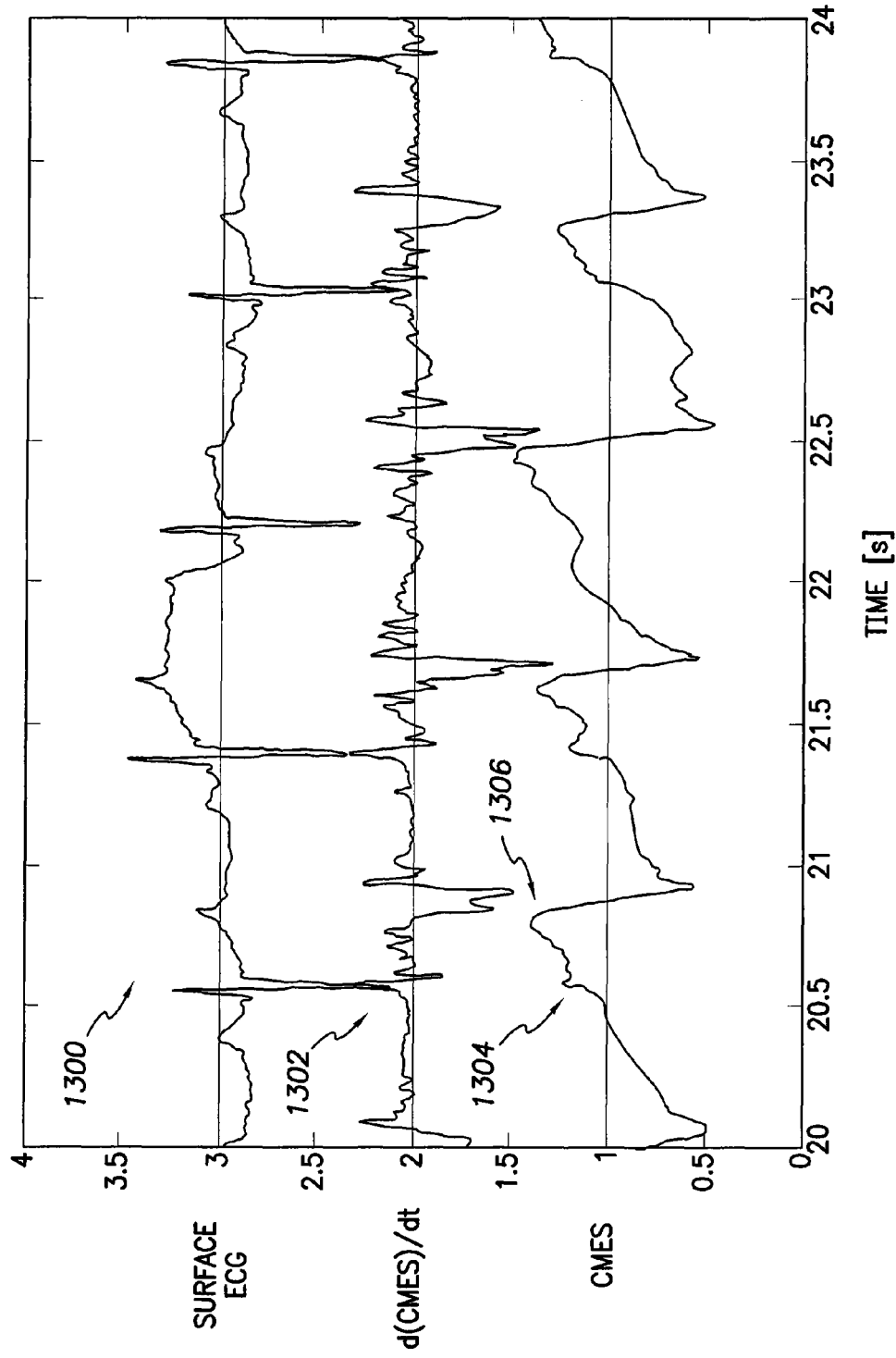
FIG. 13 shows a surface ECG, a curve representing dCMES/dt and a displacement curve derived from actual porcine data using an embodiment of a CMES in the right ventricle.

FIG. 13 represents actual porcine animal data with an embodiment of a CMES in the ring or proximal position of a pacing electrode in the RV apex, where the electrode tip is in tissue contact but the CMES is not in close contact to myocardium. The top signal is a surface ECG 1300, the middle signal is a first order derivative, dCMES/dt 1302, similar in quality and in its temporal relationship to tissue Doppler derived myocardial velocity time graphs depicted and described above (FIG. 5B). The integral of this data, CMES 1304, bottom signal, is displacement. Peak systolic RV apical displacement is identified in the figure by arrow 1306. Comparable data can be acquired from a larger surface area CMES that is basally located and parallel to the cardiac longitudinal axis. A higher fidelity signal more representative of global cardiac displacement can be derived from such a sensor. Summation averaging of multiple waveforms will provide data with improved signal to noise ratio.

Figure 14:
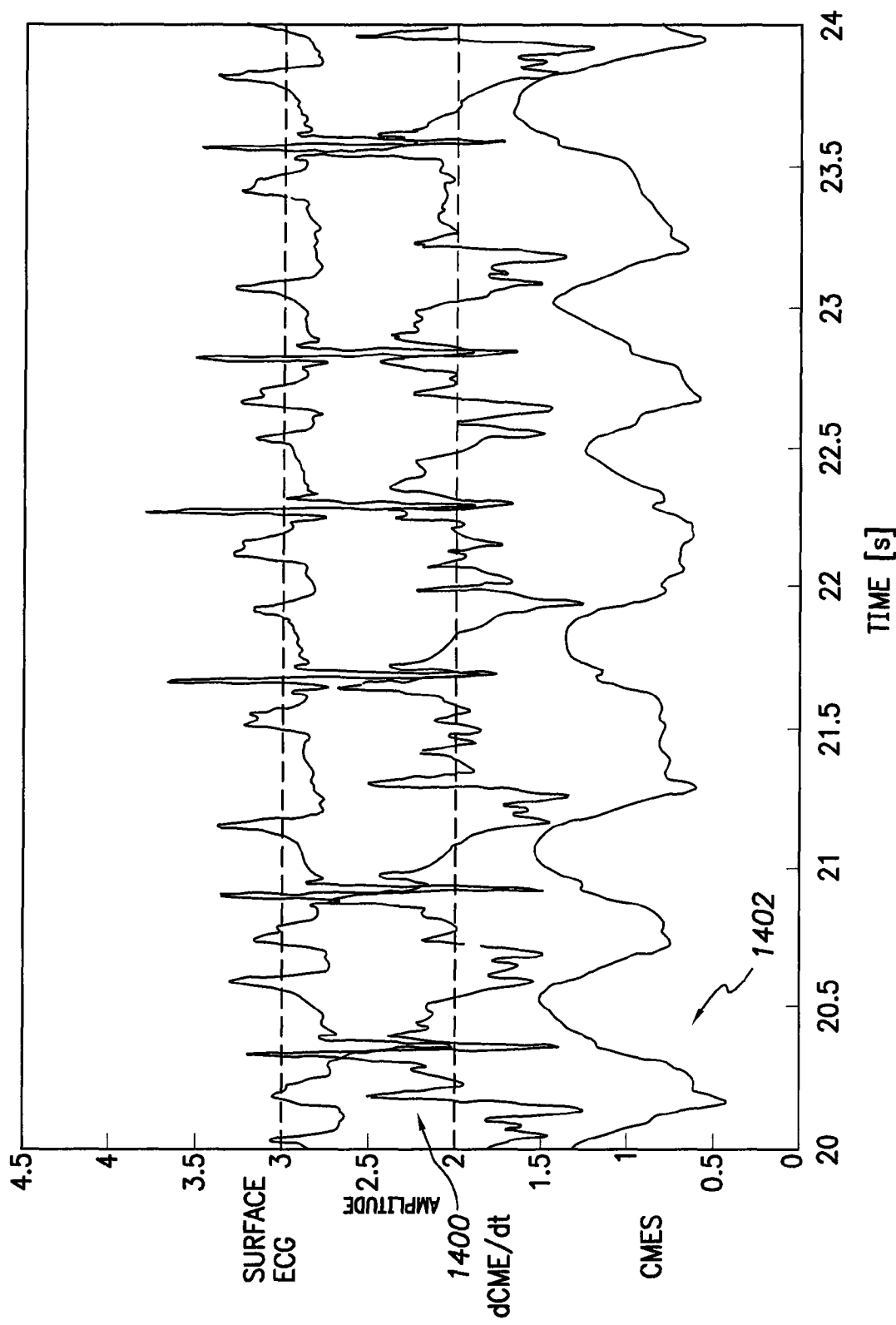
FIG. 14 shows a surface ECG, a curve representing dCMES/dt and a displacement curve derived from actual porcine data using an embodiment of a CMES in the left ventricle.
Figure 15:
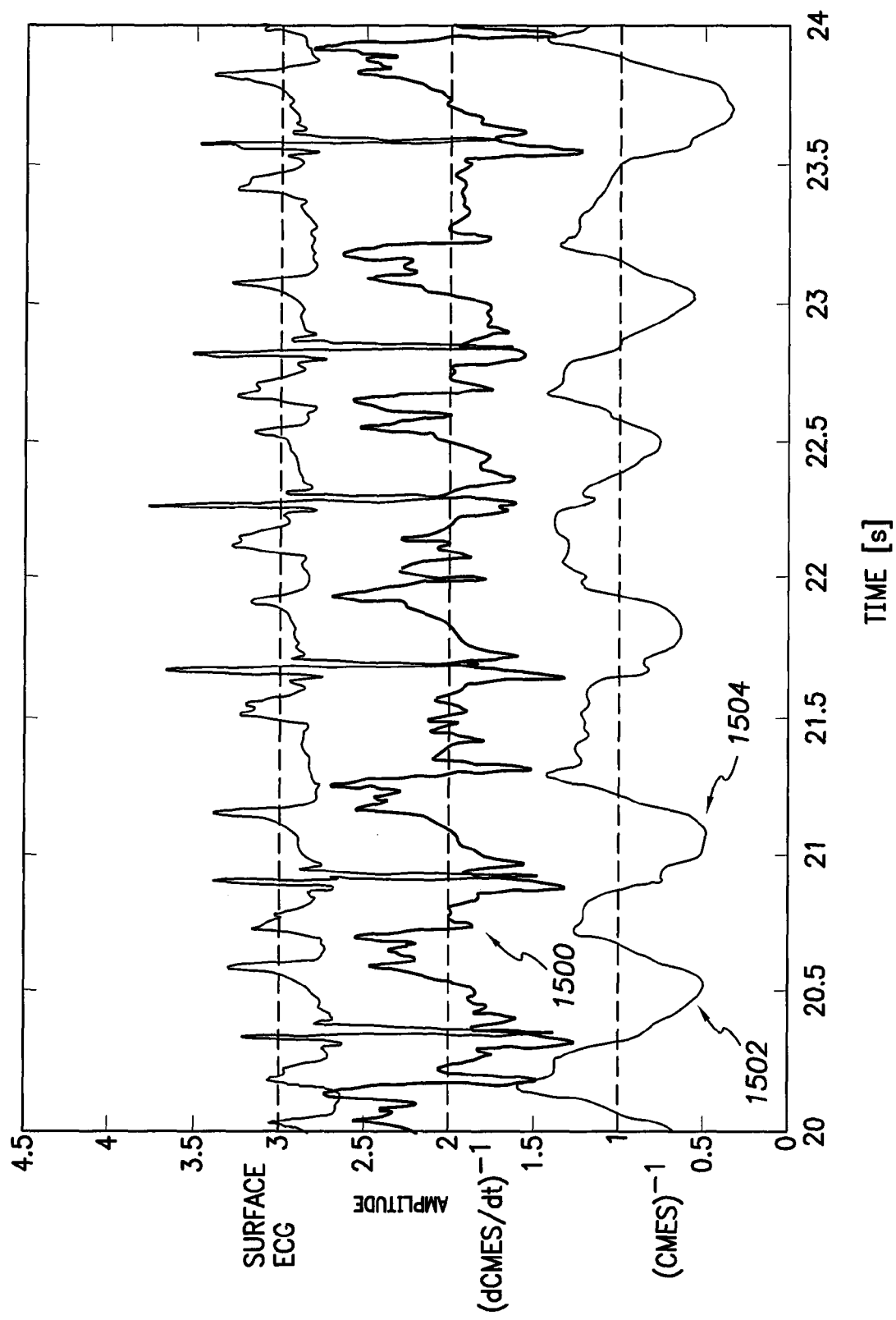
FIG. 15 shows a surface ECG, an inverted curve representing dCMES/dt and an inverted displacement curve derived from actual porcine data using an embodiment of a CMES in the left ventricle.

FIG. 14 represents actual porcine animal data with an embodiment of a CMES sensor in the LV anterior interventricular vein located ⅔ the distance from the apex toward the base parallel to the cardiac longitudinal axis. The sensor is in contact with the underlying tissue. The waveforms 1400 and 1402 derived are more representative of myocardial deformation and strain. Thus, dCMES/dt is an index of strain rate and the integral of this provides an index of strain. The strain/strain rate time graphs are similar to those acquired using tissue Doppler imaging and speckle tracking techniques described above. Inversion of the waveforms 1400 and 1402 to derive an analogous vector 1500 and 1502, as shown in FIG. 15, demonstrates waveforms similar to those depicted in FIG. 5B derived from the strain rate equation (Eq. 2) being applied to Doppler derived myocardial tissue velocity imaging performed, for example, by GE Vivid series echocardiography equipment. Arrow 1504 is peak longitudinal strain.

Second order derivatives of displacement data or first order derivatives of velocity data can be used to calculate acceleration indices as well.

Interval Specific Ensemble Averaging

Figure 16:
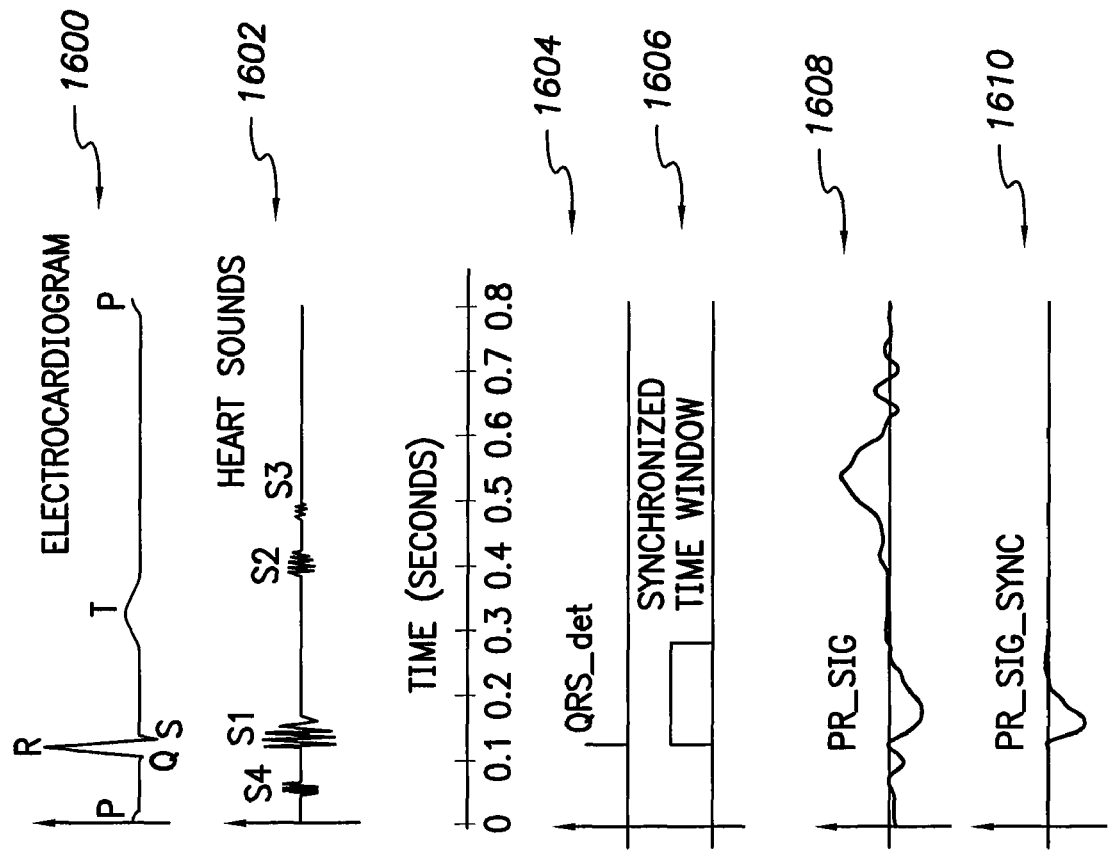
FIG. 16 shows how averaging of the measured mechanical stress waveforms can be synchronized with the detected heart events, such as spontaneous R-waves or stimulated events such as valvular heart sounds.
Figure 17:
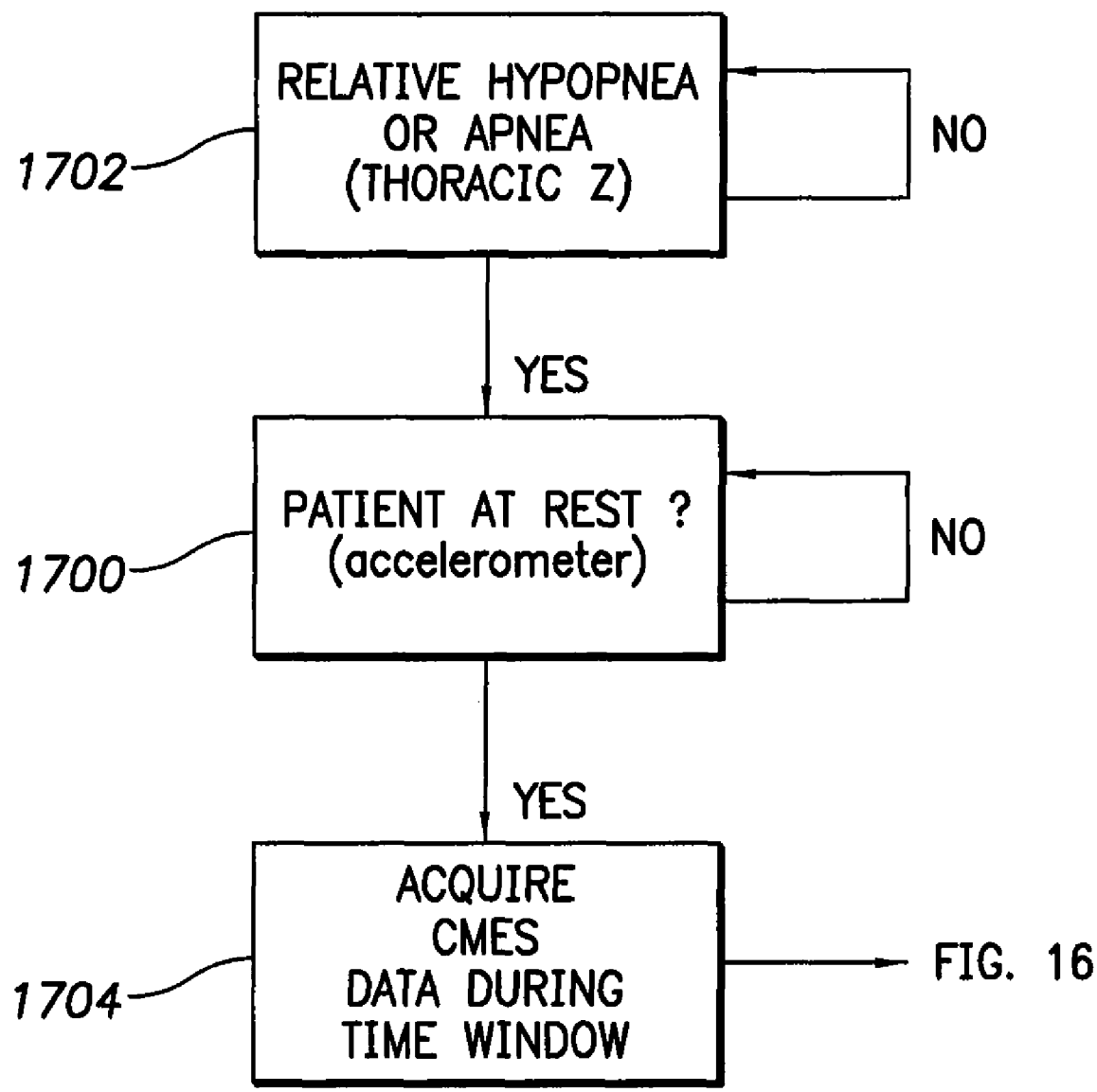
FIG. 17 is a block diagram for taking CMES measurements when the patient is in a state of relative hypopnea or apnea.

As shown in FIG. 16, averaging of the measured mechanical stress waveforms is synchronized with the detected heart events, such as spontaneous R-waves 1600 or stimulated events such as valvular heart sounds 1602 detected by an implanted sonomicrometer, filtered and/or processed CMES signal, or a signal from an alternate sensor. Synchronization of data acquisition can also be triggered by an impedance based parameter or index that relates to respiration and/or myocardial mechanics. The waveform 1608 is averaged over a predetermined number of consecutive heart cycles 1606 by taking the sample average for every time distance from the detected heart event, such as a QRS complex 1604. The number of predetermined heart cycles could for instance be 30. For example, if the sampling frequency is 1 kHz, an averaged sample value at 24 ms distance from a QRS is calculated by taking the value at 24 ms distance from a QRS for the predetermined number of heart cycles, which is 30 in this example, and then averaging the values. The averaging is repeated for all samples in the heart interval. This will result in an averaged waveform 1610 based on the predetermined number of beats (in the example 30 beats). The strain calculations are then performed using the averaged waveform 1610. The advantage is that short term variations depending on for instance respiration are cancelled out. This method of averaging is referred to as "waveform averaging". Having the advantage of enhancing details in the acquired waveform, the heart rate is preferably fairly stable during the process. This methodology can improve signal-to-noise ratio. Data acquisition during periods of rest and relative apnea or hypopnea will further improve the signal to noise ratio (SNR). As shown in FIG. 17, input from a can based accelerometer 1700, to determine whether the patient is at rest, and respirometers 1702, to determine whether the patient is in a state of apnea or hypopnea, can trigger times for CMES data acquisition 1704 and function in conjunction with the Interval Specific Ensemble Averaging feature describe herein and in FIG. 16.

Value Averaging

An alternative method to perform the averaging is to calculate the strain parameters for each non-averaged consecutive heart beat and then average the calculated parameters over the predetermined number of heart beats. This method of averaging is referred to as "value averaging." Having the advantage of detecting beat-to-beat variations of the measured parameters, the heart rate does not have to be fairly stable during the process. This is particularly suitable when variability analysis is to be performed on the measured parameters.

Other Averaging Techniques

The average calculation above is performed using consecutive heart beats, numbered 1, 2, 3 . . . , and so on. Alternatively, two average values can be calculated. For example, the first value can be calculated using odd numbered beats: 1, 3, 5 . . . , and so on. The second value can be calculated using even numbered beats: 2, 4, 6 . . . , and so on. The two averaged values can be expected to be equal, but during severe heart tissue ischemia two groups can be formed. This will be the result of the 2:1 rhythmic pattern in heart beats often seen during this condition. Other manifestations are the presence of rhythmic T-wave alternans (TWA) and pulsus alternans. Processing the measured strain in this way forms a strong detector for this condition and can serve to notify the clinician that a change in physiologic status has occurred.

What is claimed is:

1. An implantable cardiac stimulation device comprising:
a first lead adapted to be implanted in or on the heart of a patient, wherein the first lead comprises a long axis and a first mechanical sensor positioned along the long axis, the first mechanical sensor configured to obtain measurements indicative of physical contraction and relaxation of the walls of the heart during systole and diastole, wherein the first lead is adapted to be implanted with its long axis at least partially around the basal region of the heart;
a second lead adapted to be implanted in or on the heart of a patient, wherein the second lead comprises a long axis and a second mechanical sensor positioned along the long axis, the second mechanical sensor configured to obtain measurements indicative of physical contraction and relaxation of the walls of the heart during systole and diastole, wherein the second lead is adapted to be implanted with its long axis at least partially around the apical region of the heart; and
a controller configured to receive signals from the first mechanical sensor and the second mechanical sensor indicative of contraction and relaxation of the walls of the heart, calculate a basal rotational velocity index based on the signals received from the first mechanical sensor, calculate an apical rotational velocity index based on the signals received from the second mechanical sensor, and derive a torsion index based on the basal rotational velocity index and the apical rotational velocity index.

2. The device of claim 1 wherein each of the first mechanical sensor and the second mechanical sensor comprises a cardiomechanical electric sensor material (CMES) configured to contact myocardial tissue at two points separated by a distance x.

3. The device of claim 2 wherein the controller is configured to calculate the basal velocity index based on the distance x and changes in the signals received from the first mechanical sensor as a function of time (dCMES/dt).

4. The device of claim 1 wherein the first mechanical sensor is adapted to be positioned in one of the proximal to lateral portion of the main coronary sinus branch, the atrioventricular groove and the atrioventricular ring.

5. The device of claim 1 wherein the second mechanical sensor is adapted to be positioned in pericardial space around the apex of the heart.

6. The device of claim 2 wherein the controller is configured to calculate the apical velocity index based on the distance x and changes in the signals received from the second mechanical sensor as a function of time (dCMES/dt).

7. The device of claim 1 wherein the torsion index is a summation of the basal rotational velocity index and the apical rotational velocity index.

8. The device of claim 1 wherein the at least one of the first mechanical sensor and the second mechanical sensor runs in a helical fashion along the long axis of the respective first lead or second lead.

9. The device of claim 1 wherein the at least one of the first mechanical sensor and the second mechanical sensor comprises a material embedded parallel to the long axis of the respective first lead or second lead.

10. The device of claim 1 wherein the controller is further configured to monitor changes in the torsion index over time as an indication of heart failure status.

* * * * *